United States Patent
Goudriaan et al.

(10) Patent No.: US 10,544,434 B2
(45) Date of Patent: Jan. 28, 2020

(54) PROCESS FOR THE PREPARATION OF LISDEXAMFETAMINE AND RELATED DERIVATIVES

(71) Applicant: NORAMCO, INC., Athens, GA (US)

(72) Inventors: Pietertje Elisabeth Goudriaan, Roeselare (BE); Jasper Kaiser, Nijmegen (NL); Hemen Ibrahim, Nijmegen (NL); Govert Arie Verspui, Druten (NL); Douglas Phillip Cox, Eagleville, PA (US)

(73) Assignee: Noramco, Inc., Athens, GA (US)

( * ) Notice: Subject to any disclaimer, the term of this patent is extended or adjusted under 35 U.S.C. 154(b) by 0 days.

(21) Appl. No.: 15/182,698

(22) Filed: Jun. 15, 2016

(65) Prior Publication Data

US 2016/0376618 A1    Dec. 29, 2016

Related U.S. Application Data

(60) Provisional application No. 62/185,924, filed on Jun. 29, 2015.

(51) Int. Cl.
| | | |
|---|---|---|
| *C12P 13/00* | (2006.01) | |
| *C12P 41/00* | (2006.01) | |
| *C07C 231/12* | (2006.01) | |
| *C07C 233/13* | (2006.01) | |
| *C07C 237/06* | (2006.01) | |

(52) U.S. Cl.
CPC .......... *C12P 13/001* (2013.01); *C07C 233/13* (2013.01); *C07C 237/06* (2013.01)

(58) Field of Classification Search
None
See application file for complete search history.

(56) References Cited

U.S. PATENT DOCUMENTS

| | | |
|---|---|---|
| 7,233,735 B2 | 6/2007 | Mickle et al. |
| 7,655,630 B2 | 2/2010 | Mickle et al. |
| 2006/0046287 A1* | 3/2006 | Kung ............... C07C 33/46 435/135 |
| 2009/0292143 A1 | 11/2009 | Buenger et al. |
| 2011/0196173 A1 | 8/2011 | Meudt et al. |
| 2012/0157706 A1 | 6/2012 | Bauer et al. |

FOREIGN PATENT DOCUMENTS

| | | |
|---|---|---|
| WO | WO 95/08636 A1 | 3/1995 |
| WO | WO 2010/058206 A1 | 5/2010 |
| WO | WO 2010/148305 A1 | 12/2010 |

OTHER PUBLICATIONS

Wang et al. (Tetrahdron Letters, 37 (30):5317-5320, 1996).*
Sethi et al. (Journal of Molecular Catalysis B: Enzymatic 108 (2014) 77-81).*
Miyazawa et al., J. Chem Soc. PerkinTrans 1, (2002), 390-395.
Pera et al., Tetrahedron Letters, vol. 37, 3609-3612 (1996).
Munoz et al., Organic and Biomolecular Chemistry, (2011), pp. 8171-8177, vol. 9, nb: 23.
Gonzalez-Sabin et al., Tetrahedron Asymmetry, (2000), pp. 1315-1320, vol. 13.
Reddy et al., "An improved process for the preparation of lisdexamfetamine and its pharmaceutically acceptable salts (Abstract)," CAPLUS; STN Database accession No. 2012-654913, (2012).
Nechab et al., "N-acyl glycinates as acyl donors in serine protease-catalyzed kinetic resolution of amines. Improvement of selectivity and reaction rate," Org. Biomol. Chem., 6(21): 3917-3920, (2008).
Ismail et al., "A green, fully enzymatic procedure for amine resolution, using a lipase and penicillin G acylase," Green Chemistry, 10(4): 415 (2008).
International Search Report and Written Opinion for International Application No. PCT/US2016/038066, dated Dec. 9, 2016.

\* cited by examiner

*Primary Examiner* — Bong-Sook Baek
(74) *Attorney, Agent, or Firm* — Alston & Bird, LLP

(57) ABSTRACT

The present invention is directed to processes for the preparation of lisdexamfetamine and related derivatives, wherein the processes comprise coupling to racemic or enantiomerically enriched amphetamine and wherein the resulting product is advantageously enantiomerically or diastereomerically enriched in the desired stereoisomer.

29 Claims, No Drawings

PROCESS FOR THE PREPARATION OF LISDEXAMFETAMINE AND RELATED DERIVATIVES

CROSS-REFERENCE TO RELATED APPLICATION

The present application claims the benefit of the earlier filing date of U.S. provisional patent application 62/185,924, filed Jun. 29, 2015, the entirety of which application is hereby incorporated by reference herein as if fully set forth herein.

FIELD OF THE INVENTION

The present invention is directed to processes for the preparation of lisdexamfetamine and related derivatives, wherein the processes comprise coupling to racemic or enantiomerically enriched amphetamine and wherein the resulting product is advantageously enantiomerically or diastereomerically enriched in the desired stereoisomer

BACKGROUND OF THE INVENTION

Lisdexamfetamine dimesylate is approved and marketed in the United States for the treatment of attention-deficit hyperactivity disorder in pediatric patients. The active compound lisdexamfetamine contains D-amphetamine covalently linked to the essential amino acid L-lysine. Controlled release of D-amphetamine, a psychostimulant, occurs following administration of lisdexamfetamine to a patient. The controlled release has been reported to occur through hydrolysis of the amide bond linking D-amphetamine and L-lysine.

A procedure for making lisdexamfetamine hydrochloride is described in U.S. Pat. No. 7,223,735 to Mickle et al. (hereinafter Mickle). The procedure involves reacting D-amphetamine with (S)-2,5-dioxopyrrolidin-1-yl 2,6-bis(tert-butoxycarbonylamino)hexanoate to form a lysine amphetamine bearing tert-butylcarbamate protecting groups. This intermediate is treated with hydrochloric acid to remove the tert-butylcarbamate groups and provide lisdexamfetamine as its hydrochloride salt. In a subsequent publication, U.S. Pat. No. 7,655,630 Mickle et al. describe the conversion of the lysine amphetamine bearing tert-butylcarbamate protecting groups to the final dimesylate salt by treatment with methanesulfonic acid. A different procedure to link D-amphetamine to the 2,6-bis(tert-butoxycarbonylamino)hexanoate is described in U.S. Pat application No 2011/0196173 A1 to Meudt et al. (hereinafter Meudt). The procedure involves reacting D-amphetamine with 2,6-bis(tert-butoxycarbonylamino)hexanoic acid in the presence of an alkylphosphonic anhydride to form a lysine amphetamine bearing tert-butylcarbamate protecting groups and cleaving the protecting groups in a one-pot reaction or in two or more separate steps.

Another procedure for converting amphetamine enriched in the dextro-enantiomer (at least 90%) is described in US 2012/0157706 A1 to Bauer et al., (hereinafter Bauer). The procedure involves reacting amphetamine having an enantiomeric ratio of less than 99:1 (D-amphetamine to L-amphetamine) with (S)-2,5-dioxopyrrolidin-1-yl 2,6-bis(benzyloxycarbonylamino)hexanoate to form a lysine amphetamine bearing benzylcarbamate protecting groups. The lysine amphetamine bearing benzylcarbamate protecting groups is further purified by crystallizing from a mixture comprising (i) at least one of a $C_1$-$C_4$ aliphatic alcohol, $C_1$-$C_4$ aliphatic carboxylic acid, aliphatic tertiary amine, or water, and (ii) ($C_1$-$C_4$ alkyl)-$CO_2$($C_1$-$C_4$ alkyl), to provide the lysine-amphetamine compound in up to purity of at least 99.95% (w/w), when starting with a mixture of D-amphetamine and L-amphetamine having an enantiomeric ratio of less than 99:1 (D-amphetamine to L-amphetamine). The purified lysine amphetamine bearing benzylcarbamate protecting groups is converted to lisdexamfetamine dimesylate by catalytic hydrogenation to remove the benzyloxy protecting groups and subsequent addition of methanesulfonic acid to generate the final product.

The routes described above for the preparation of lisdexamfetamine start from enantiomerically pure D-amphetamine or D-amphetamine which is enriched to at least 90:10 (D-amphetamine to L-amphetamine). D-amphetamine is in turn prepared from racemic amphetamine by enantiomeric resolution of a diastereomeric salt using a chiral acid (e.g. tartaric acid) or by a multi-step synthesis from expensive raw materials 1R,2S-(−)-norephedrine or 1R,2S-(+)-norpseudoephedrine. A procedure for making D-amphetamine from either 1R,2S-(−)-norephedrine or 1R,2S-(+)-norpseudoephedrine is described in U.S. Pat. No. 6,399,828 to Boswell and Lo (hereinafter Boswell). The procedure involves converting the 1R,2S-(−)-norephedrine or 1R,2S-(+)-norpseudoephedrine to the corresponding 0-acetyl-phenylpropanolamine salt, followed by catalytic hydrogenation to D-amphetamine salt. A variation of this procedure is described in U.S. Patent application 2009/0292143 A1 to Buenger et al. (hereinafter Buenger). The procedure involves converting the 1R,2S-(−)-norephedrine or 1R,2S-(+)-norpseudoephedrine to the corresponding 1-chloro-1-phenyl-2-propanolamine salt, treating the 1-chloro-1-phenyl-2-propanolamine salt with activated carbon followed by catalytic hydrogenation to D-amphetamine salt. Yet another variation of this procedure is described in WO 2010/058206 A1 to Fishbein and Mencel (hereinafter Fishbein). The procedure involves converting catalytic hydrogenation of the oxazolidine of 1R,2S-(−)-norephedrine or 1R,2S-(+)-norpseudoephedrine to D-amphetamine.

A hybrid approach to lisdexamfetamine starting from 1R,2S-(−)-norephedrine is described in WO 2010/148305 A1 to Jass et al. (hereinafter Jass). 1R,2S-(−)-norephedrine was first converted to the corresponding 1-chloro compound with thionyl chloride and the resulting chloro-D-amphetamine hydrochloride was coupled with a bis-protected lysine to give a bis-protected chloro-lisdexamfetamine intermediate. The bis-protected chloro-lisdexamfetamine was converted to the corresponding bis-protected lisdexamfetamine by catalytic hydrogenation, and then converted to lisdexamfetamine dimesylate by treatment with methanesulfonic acid.

Furthermore, the coupling of the amphetamine to the protected lysine amino acid derivative for each of these methods requires either an expensive leaving group such as the N-hydroxysuccinimide ester attached to the carboxyl group of the protected lysine amino acid to promote amide coupling conditions or other reagents used to activate a carboxylic acid group for reaction with an amine (e.g., D-amphetamine) include, for example, carbodiimides (such as dicyclohexylcarbodiimide; N,N'-diisopropylcarbodiimide, and 1-ethyl-3-(3-dimethylaminopropyl) carbodiimide), phosphonium reagents (such as benzotriazol-1-yloxytris(dimethylamino)phosphonium hexafluorophosphate), uronium reagents (2-(1H-benzotriazole-1-yl)-1,1,3,3-tetramethyluronium hexafluorophosphate), anhydrous 1-hydroxybenzotriazole, and phosphonic acid anhydrides (such as propane phosphonic acid anhydride, sold under the tradename T3P®).

A shorter, more cost-effective route would be provided by selective conversion of racemic amphetamine to lisdexamfetamine by taking advantage of the chirality of the protected lysine amino acid derivative. Miyazawa et al., *J. Chem Soc. Perkin Trans* 1, 2002, 390-395 describe the α-chymotrypsin catalyzed conversion of a racemic amine and N—Z—(S)-phenylalanine esters to give primarily the S,S-diastereomer of the resulting amide. Pera et al., *Tetrahedron Letters*, Vol 37, 3609-3612 (1996) describe the papain catalyzed conversion of a racemic amino acid ester (Z-γ,γ'-di-tert-butyl-D,L-Carboxyglutamic acid, methylester) with a chiral amino acid to give the diastereomerically pure L-carboxyglutamic acid-containing dipeptide while the D-Carboxyglutamic acid, methylester remained in the solution unreacted.

MUNOZ et al., in Organic and Biomolecular Chemistry, 2011, pp 8171-8177, Vol. 9, nb: 23 describe enzymatic enantiomeric resolution of phenylethylamines (structurally related to amphetamine. However, the resolution described by MUNOZ et al. is directed to compounds which (unlike lisdexamfetamine) contain only a single stereo-center. GONZALEZ-SABIN et al., in Tetrahedron Asymmetry, 2000, pp 1315-1320, Vol. 13 describe CAL-B-catalyzed resolution of β-substituted isopropylamines. However, GONZALEZ-SABIN describe the use of *Candida antarctica* lipase B for enantioselective acylation of racemic amines, wherein the major enantiomer product is the (R)-amide.

There remains a need for new methods for the preparation of lisdexamfetamine and salts thereof, wherein the lisdexamfetamine is prepared with high enantiomeric/diastereomeric purity. The present invention addresses this need and further, provides one or more additional process advantages, as described in more detail hereinafter.

SUMMARY OF THE INVENTION

The present invention is directed to a process for the preparation of a diastereomerically enriched amphetamine derivative, a compound of formula (X)

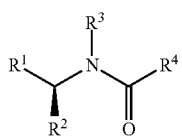

wherein
$R^1$ is selected from the group consisting of phenyl and benzyl; wherein the phenyl or benzyl is optionally substituted with one to three substituents independently selected from the group consisting of $C_{1-4}$alkyl and $C_{1-4}$alkoxy;
$R^2$ is selected from the group consisting of $C_{1-5}$alkyl;
$R^3$ is selected from the group consisting of hydrogen and $C_{1-4}$alkyl;
$R^4$ is an amino acid radical;
or a pharmaceutically acceptable salt thereof; comprising

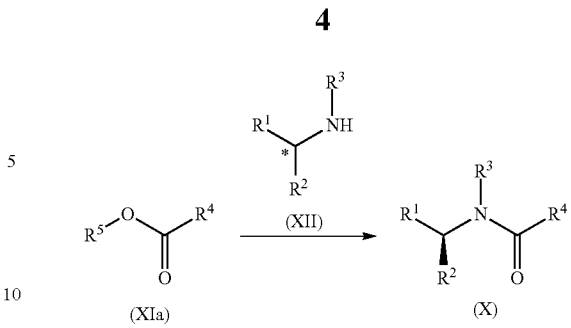

reacting a compound of formula (XIa), wherein $R^5$ is selected from the group consisting of hydrogen and $C_{1-12}$alkyl with a compound of formula (XII); wherein the compound of formula (XII) is racemic or is present in an enantiomeric excess of one of its corresponding enantiomers (preferably the D-enantiomer); in the presence of an S-selective enzyme catalyst neat or in a solvent; to yield the corresponding compound of formula (X); wherein the compound of formula (X) is present in an enantiomeric excess (preferably in an enantiomeric excess of at least about 60%, more preferably, in an enantiomeric excess of at least 75%, more preferably in an enantiomeric excess of at least 80%).

The present invention is further directed to a process for the preparation of a diastereomerically enriched amphetamine derivative, a compound of formula (X)

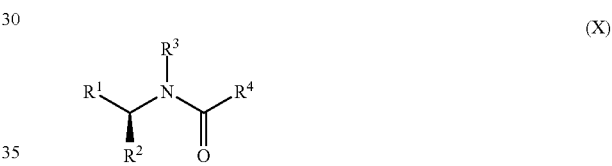

wherein
$R^1$ is selected from the group consisting of phenyl and benzyl; wherein the phenyl or benzyl is optionally substituted with one to three substituents independently selected from the group consisting of $C_{1-4}$alkyl and $C_{1-4}$alkoxy;
$R^2$ is selected from the group consisting of $C_{1-5}$alkyl;
$R^3$ is selected from the group consisting of hydrogen and $C_{1-4}$alkyl;
$R^4$ is an amino acid radical;
or a pharmaceutically acceptable salt thereof; comprising

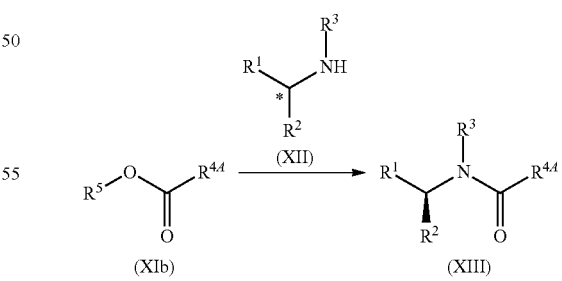

reacting a compound of formula (XIb), wherein $R^{4A}$ is a nitrogen-protected amino acid radical, and wherein $R^5$ is selected from the group consisting of hydrogen and $C_{1-12}$alkyl with a compound of formula (XII); wherein the compound of formula (XII) is racemic or is present in an enantiomeric excess of one of its corresponding enantiomers (preferably the D-enantiomer); in the presence of an S-selective enzyme catalyst; neat or in a solvent; to yield the corresponding compound of formula (XIII); wherein the compound of formula (XIII) is present in an enantiomeric excess (preferably in an enantiomeric excess of at least about 60%, more preferably, in an enantiomeric excess of at least 75%, more preferably in an enantiomeric excess of at least 80%);

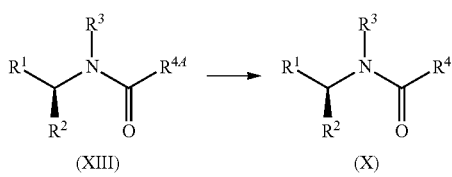

de-protecting the compound of formula (XIII); to yield the corresponding compound of formula (X); wherein the compound of formula (X) is present in an enantiomeric excess (preferably in an enantiomeric excess of at least about 60%, more preferably, in an enantiomeric excess of at least 75%, more preferably in an enantiomeric excess of at least 80%).

The present invention is further directed to a process for the preparation of a compound of formula (I), also known as lisdexamfetamine,

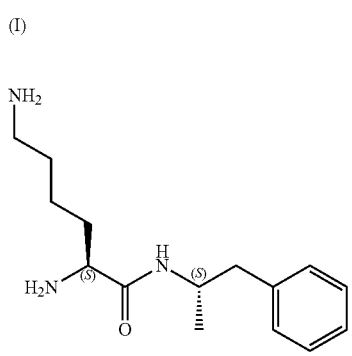

or a pharmaceutically acceptable salt thereof; comprising the steps of

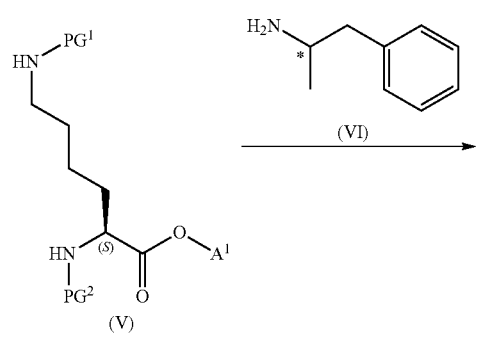

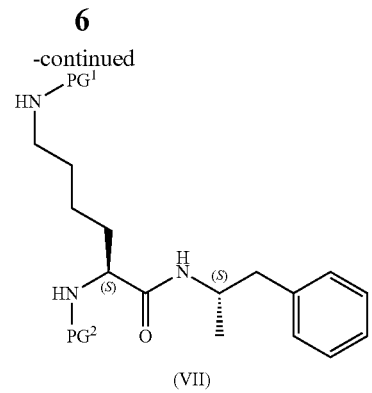

reacting a compound of formula (V), wherein $PG^1$ is a first nitrogen protecting group, wherein $PG^2$ is a second nitrogen protecting group and wherein $A^1$ is selected from the group consisting of $C_{1-12}$alkyl, with a compound of formula (VI) (also known as amphetamine or 1-phenylpropan-2-amine); wherein the compound of formula (IV) is racemic or is present in an enantiomeric excess of one of its corresponding enantiomers (preferably the D-enantiomer); in the presence of an S-selective enzyme catalyst; wherein the S-selective enzyme catalyst is not a natural lipase; neat or in a solvent; to yield the corresponding compound of formula (VII); wherein the compound of formula (VII) is present in a diastereomeric excess (preferably in a diastereomeric a diastereomeric excess of at least about 60%, more preferably, in a diastereomeric excess of at least 75%, more preferably in a diastereomeric excess of at least 80%);

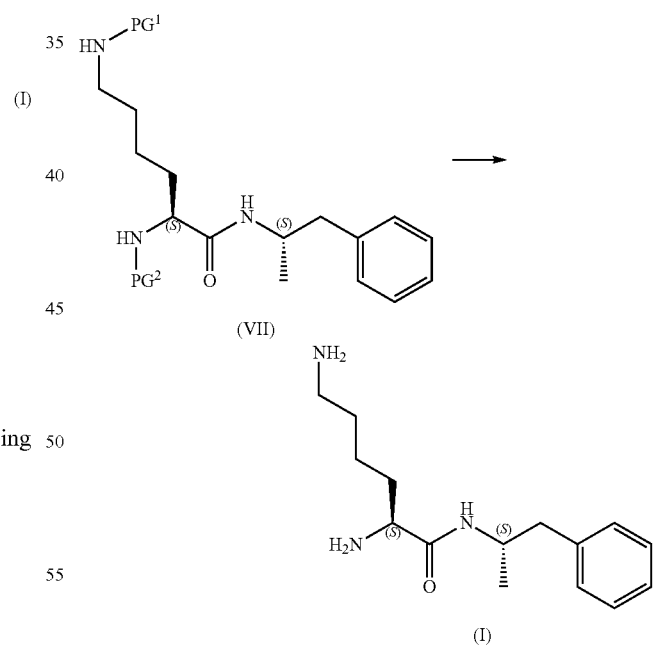

de-protecting the compound of formula (VII), to yield the corresponding compound of formula (I); wherein the compound of formula (I) is present in a diastereomeric excess (preferably in a diastereomeric excess of at least about 60%, more preferably, in a diastereomeric excess of at least 75%, more preferably in a diastereomeric excess of at least 80%).

The present invention is further directed to a process for the preparation of pharmaceutically acceptable salts of lisdexamfetamine, preferably the dimesylate salt of lisdexamfetamine, as described in more detail herein.

The present invention is further directed to a process for the preparation of a diastereomerically enriched a compound of formula (XX)

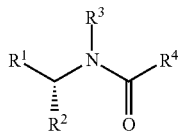

wherein

R¹ is selected from the group consisting of phenyl and benzyl; wherein the phenyl or benzyl is optionally substituted with one to three substituents independently selected from the group consisting of $C_{1-4}$alkyl and $C_{1-4}$alkoxy;

R² is selected from the group consisting of $C_{1-5}$alkyl;

R³ is selected from the group consisting of hydrogen and $C_{1-4}$alkyl;

R⁴ is an amino acid radical;

or a pharmaceutically acceptable salt thereof; comprising

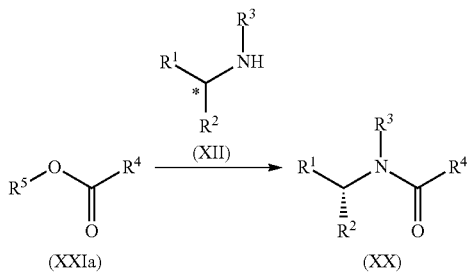

reacting a compound of formula (XXIa), wherein R⁵ is selected from the group consisting of hydrogen and $C_{1-12}$alkyl with a compound of formula (XII); wherein the compound of formula (XII) is racemic or is present in an enantiomeric excess of one of its corresponding enantiomers in the presence of an R-selective enzyme catalyst; neat or in a solvent; to yield the corresponding compound of formula (XX); wherein the compound of formula (XX) is present in an enantiomeric excess (preferably in an enantiomeric excess of at least about 60%, more preferably, in an enantiomeric excess of at least 75%, more preferably in an enantiomeric excess of at least 80%).

The present invention is further directed to a process for the preparation of a diastereomerically enriched compound of formula (XX)

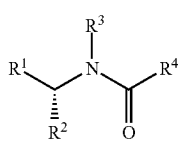

wherein

R¹ is selected from the group consisting of phenyl and benzyl; wherein the phenyl or benzyl is optionally substituted with one to three substituents independently selected from the group consisting of $C_{1-4}$alkyl and $C_{1-4}$alkoxy;

R² is selected from the group consisting of $C_{1-5}$alkyl;

R³ is selected from the group consisting of hydrogen and $C_{1-4}$alkyl;

R⁴ is an amino acid radical;

or a pharmaceutically acceptable salt thereof; comprising

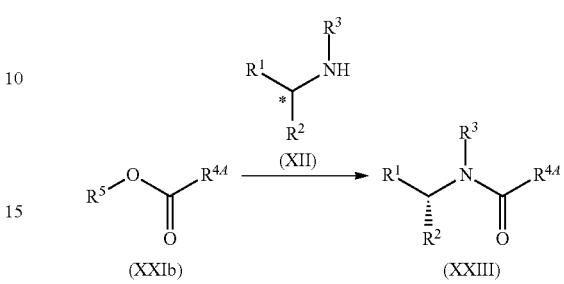

reacting a compound of formula (XXIb), wherein $R^{4A}$ is a nitrogen-protected amino acid radical, and wherein R⁵ is selected from the group consisting of hydrogen and $C_{1-12}$alkyl with a compound of formula (XII); wherein the compound of formula (XII) is racemic or is present in an enantiomeric excess of one of its corresponding enantiomers; in the presence of an R-selective enzyme catalyst; neat or in a solvent; to yield the corresponding compound of formula (XXIII), wherein the compound of formula (XIII) is present in an enantiomeric excess (preferably in an enantiomeric excess of at least about 60%, more preferably, in an enantiomeric excess of at least 75%, more preferably in an enantiomeric excess of at least 80%);

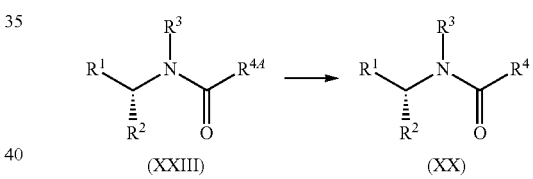

de-protecting the compound of formula (XXIII), to yield the corresponding compound of formula (XX); wherein the compound of formula (XX) is present in an enantiomeric excess (preferably in an enantiomeric excess of at least about 60%, more preferably, in an enantiomeric excess of at least 75%, more preferably in an enantiomeric excess of at least 80%).

The present invention is further directed to a product prepared according to any of the process(es) described herein.

Illustrative of the invention is a pharmaceutical composition comprising a pharmaceutically acceptable carrier and the product prepared according to any of the process(es) described herein. An illustration of the invention is a pharmaceutical composition made by mixing the product prepared according to any of the process(es) described herein and a pharmaceutically acceptable carrier. Illustrating the invention is a process for making a pharmaceutical composition comprising mixing the product prepared according to any of the process(es) described herein and a pharmaceutically acceptable carrier.

In an embodiment, the present invention is directed to a product prepared according to any of the process(es) described herein for use as a medicament. In another embodiment, the present invention is directed to a product prepared according to any of the process(es) described herein for use in the treatment of attention deficit hyperactivity disorder (ADHD), major depressive disorder, cognitive impairment associated with schizophrenia, excessive daytime sleepiness or binge eating disorder. In another embodiment, the present invention is directed to a composition comprising a product prepared according to any of the process(es) described herein for the treatment of attention deficit hyperactivity disorder (ADHD), major depressive disorder, cognitive impairment associated with schizophrenia, excessive daytime sleepiness or binge eating disorder.

Another example of the invention is the use of a product prepared according to any of the process(es) described herein in the preparation of a medicament for treating: (a) attention deficit hyperactivity disorder (ADHD), (b) major depressive disorder, (c) cognitive impairment associated with schizophrenia, (d) excessive daytime sleepiness, (e) binge eating disorder, in a subject in need thereof. In another example, the present invention is directed to a product prepared according to any of the process(es) described herein for use in a methods for treating attention deficit hyperactivity disorder (ADHD), major depressive disorder, cognitive impairment associated with schizophrenia, excessive daytime sleepiness or binge eating disorder, in a subject in need thereof.

DETAILED DESCRIPTION OF THE INVENTION

The present invention is directed to processes for the preparation of diastereomerically enriched compounds of formula (X)

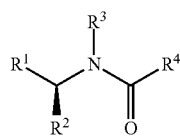

(X)

and pharmaceutically acceptable salts thereof, as described in more detail herein. The present invention is further directed to processes for the preparation of diastereomerically enriched compounds of formula (XX)

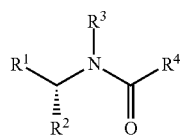

(XX)

and pharmaceutically acceptable salts thereof, as described in more detail herein.

The present invention is further directed to processes for the preparation of lisdexamfetamine, pharmaceutically acceptable salts thereof and derivatives thereof, as described in more detail herein.

More particularly, the present invention is directed to a process for the preparation of lisdexamfetamine or lisdexamfetamine dimesylate comprising S-selected enzyme catalyzed coupling of protected L-lysine with racemic amphetamine; wherein the product is diastereomerically enriched with lisdexamfetamine. In an embodiment, the present invention is directed to a process for the preparation of lisdexamfetamine dimesylate, useful for the treatment of attention deficit hyperactivity disorder (ADHD) in children and adults.

In certain embodiments, the process(es) of the present invention (for example the process(es) for the preparation of lisdexamfetamine and pharmaceutically acceptable salts thereof), use racemic amphetamine, yet nonetheless result in high diastereoselectivity in the final product. This provides a cost/and or handling advantage over previously disclosed processes, particularly for large scale/commercial manufacture. Additionally, in certain embodiments, the process(es) of the present invention, allow for the use of a relatively inexpensive carboxylic acid or alkyl ester coupling reaction (for example, a methyl ester coupling reaction), rather than the more expensive activated esters or coupling agents of previously disclosed processes.

In an embodiment, the present invention is directed to a process for the preparation of a compound of formula (X) wherein $R^1$ is selected from the group consisting of benzyl, 2-methylphenyl, 3-methylphenyl, 4-methylphenyl, 2-methoxyphenyl, 3-methoxyphenyl and 4-methoxyphenyl. In another embodiment, the present invention is directed to a process for the preparation of a compound of formula (X) wherein $R^1$ is benzyl.

In an embodiment, the present invention is directed to a process for the preparation of a compound of formula (X) wherein $R^2$ is selected from the group consisting of $C_{1-5}$alkyl. In another embodiment, the present invention is directed to a process for the preparation of a compound of formula (X) wherein $R^2$ is selected from the group consisting of methyl, ethyl, isopropyl and t-butyl. In another embodiment, the present invention is directed to a process for the preparation of a compound of formula (X) wherein $R^2$ is selected from the group consisting of methyl and ethyl. In another embodiment, the present invention is directed to a process for the preparation of a compound of formula (X) wherein $R^2$ is methyl.

In an embodiment, the present invention is directed to a process for the preparation of a compound of formula (X) wherein $R^3$ is selected from the group consisting of hydrogen and $C_{1-3}$alkyl. In an embodiment, the present invention is directed to a process for the preparation of a compound of formula (X) wherein $R^3$ is selected from the group consisting of hydrogen, methyl and ethyl. In another embodiment, the present invention is directed to a process for the preparation of a compound of formula (X) wherein $R^3$ is hydrogen or methyl.

In an embodiment, the present invention is directed to a process for the preparation of a compound of formula (X) wherein $R^4$ is selected from the group consisting of an amino acid radical and a nitrogen-protected amino acid radical. In another embodiment, the present invention is directed to a process for the preparation of a compound of formula (X) wherein $R^4$ is $PG^A$-NH—$(CH_2)_4$—CH(NH-$PG^B$), wherein each of $PG^A$ and $PG^B$ are each an independently selected nitrogen protecting group. In another embodiment, the present invention is directed to a process for the preparation of a compound of formula (X) wherein $R^4$ is $PG^A$-NH—$(CH_2)_4$—CH(NH-$PG^B$), and wherein each of $PG^A$ and $PG^B$ are the same and are a suitably selected nitrogen protection group, preferably a nitrogen protecting group selected from Boc, CBz, Alloc or Cinnoc, more preferably, $PG^A$ and $PG^B$ are the same and are Boc or CBz.

In an embodiment, the present invention is directed to a process for the preparation of a compound of formula (X) wherein $R^5$ is selected from the group consisting of hydrogen $C_{1-6}$alkyl. In another embodiment, the present invention is directed to a process for the preparation of a compound of formula (X) wherein $R^5$ is selected from the group consisting of hydrogen and $C_{1-3}$alkyl. In another embodiment, the present invention is directed to a process for the preparation of a compound of formula (X) wherein $R^5$ is selected from the group consisting of hydrogen, methyl and ethyl. In another embodiment, the present invention is directed to a process for the preparation of a compound of formula (X) wherein $R^5$ is selected from the group consisting of hydrogen and methyl. In another embodiment, the present invention is directed to a process for the preparation of a compound of formula (X) wherein $R^5$ is hydrogen. In another embodiment, the present invention is directed to a process for the preparation of a compound of formula (X) wherein $R^5$ is methyl.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{X-Y}$alkyl" wherein X and Y are integers, shall mean a carbon chain composition of between X and Y carbon atoms. For example, "$C_{1-4}$Alkyl" shall mean any straight or branched chain composition of between 1 and 4 carbon atoms (including methyl, ethyl, n-propyl, isopropyl, n-butyl, isobutyl and t-butyl).

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "$C_{X-Y}$alkoxy" wherein X and Y are integers, shall mean an oxygen ether radical of the above described straight or branched chain carbon chain composition of between X and Y carbon atoms. For example, "$C_{1-4}$alkoxy" shall mean any oxygen ether radical of the above described straight or branched chain composition of between 1 and 4 carbon atoms.

As used herein, the term "amino acid" shall mean a compound selected from the group consisting of glycine, alanine, valine, leucine, isoleucine, phenylalanine, proline, serine, threonine, tyrosine, cysteine, methionine, lysine, arginine, histidine, tryptophan, aspartic acid, glutamic acid, asparagine and glutamine.

In an embodiment of the present invention, the amino acid is selected from the group consisting of glycine, alanine, valine, leucine, isoleucine, phenylalanine, proline, serine, cysteine, methionine, aspartic acid and glutamic acid. In another embodiment of the present invention, the amino acid is selected from the group consisting of glycine, alanine, valine, leucine, isoleucine, phenylalanine and proline. In another embodiment of the present invention, the amino acid is selected from the group consisting of glycine, alanine, valine, leucine, isoleucine and phenylalanine. In another embodiment of the present invention, the amino acid is lysine.

As used herein, the term "amino acid radical" shall mean an amino acid selected from the group consisting of glycine, alanine, valine, leucine, isoleucine, phenylalanine, proline, serine, threonine, tyrosine, cysteine, methionine, lysine, arginine, histidine, tryptophan, aspartic acid, glutamic acid, asparagine and glutamine, wherein the carboxy portion of the amino acid group is removed. More particularly, the amino acid radical is selected from the group consisting of the following structures:

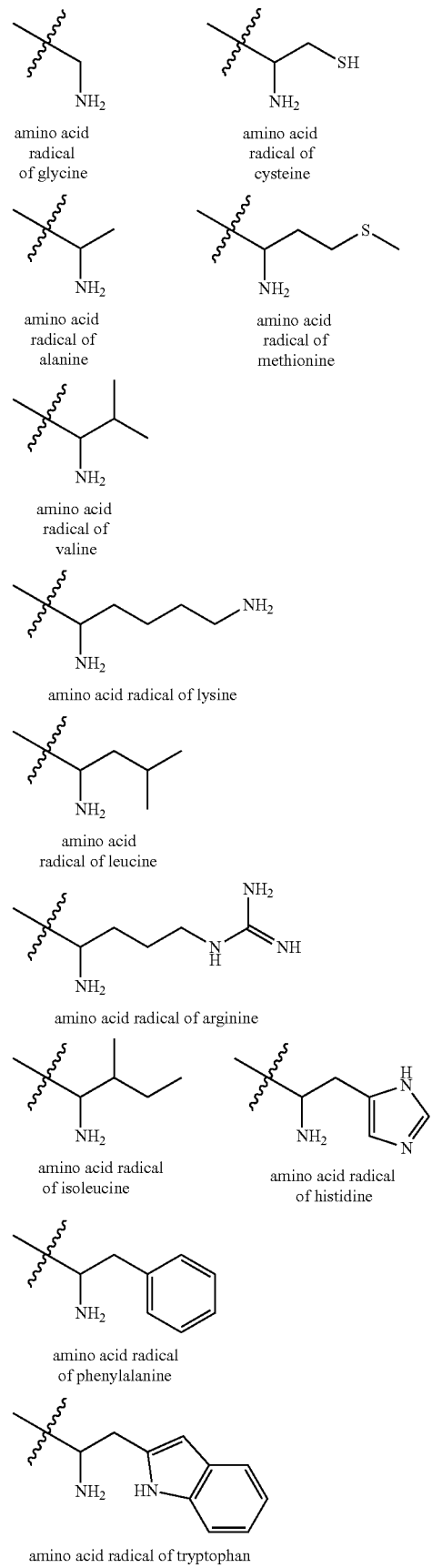

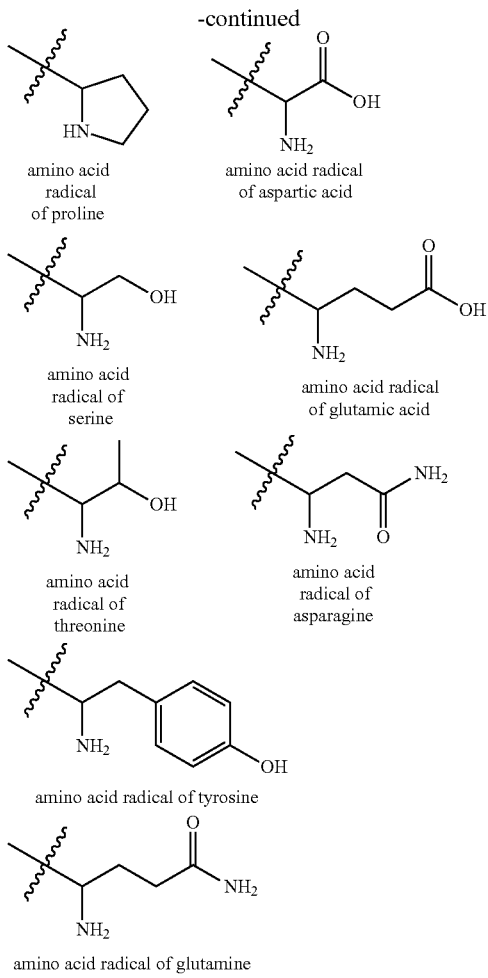

In an embodiment of the present invention, the amino acid radical is selected from the group consisting of amino acid radical of glycine, amino acid radical of alanine, amino acid radical of valine, amino acid radical of leucine, amino acid radical of isoleucine, amino acid radical of phenylalanine, amino acid radical of proline, amino acid radical of serine, amino acid radical of cysteine, amino acid radical of methionine, amino acid radical of aspartic acid and amino acid radical of glutamic acid.

In another embodiment of the present invention, the amino acid radical is selected from the group consisting of amino acid radical of glycine, amino acid radical of alanine, amino acid radical of valine, amino acid radical of leucine, amino acid radical of isoleucine, amino acid radical of phenylalanine and amino acid radical of proline.

In another embodiment of the present invention, the amino acid radical is selected from the group consisting of amino acid radical of glycine, amino acid radical of alanine, amino acid radical of valine, amino acid radical of leucine, amino acid radical of isoleucine and amino acid radical of phenylalanine.

In another embodiment of the present invention, the amino acid radical is the amino acid radical of lysine.

As used herein, the term "nitrogen-protected amino acid radical" shall mean any amino acid radical as defined herein, wherein at one or more of the nitrogen atoms present in the amino acid radical is substituted with a suitably selected nitrogen protecting groups. In an embodiment, one nitrogen atom present in the amino acid radical is substituted with a suitably selected nitrogen protecting groups. In another embodiment, each of the nitrogen atoms present in the amino acid radical is substituted with a suitably selected nitrogen protecting groups. In an embodiment, the nitrogen protecting group(s) on the nitrogen-protected amino acid radical are each independently selected from the group consisting of Boc, CBz, Alloc and Cinnoc; preferably, Boc or CBz. In another embodiment (wherein the amino acid radical contains two or more nitrogen atoms, and wherein two or more of said nitrogen atoms are substituted with a suitably selected nitrogen protecting group), the nitrogen protecting groups are the same and are selected from the group consisting of Boc, CBz, Alloc and Cinnoc, preferably Boc or CBz.

In an embodiment of the present invention, the nitrogen-protected amino acid radical is a nitrogen-protected amino acid radical of lysine, wherein the nitrogen-protected amino acid radical of lysine contains two nitrogen protecting groups, and wherein the two nitrogen protecting groups are the same and are selected from the group consisting of Boc, CBz, Alloc and Cinnoc (preferably, the two nitrogen protecting groups are the same and are selected from the group consisting of Boc and CBz).

One skilled in the art will recognize that wherein the amino acid radical contains additional reactive groups, such as an O atom (for example, as a terminal OH group) or a S atom (for example, as a terminal SH group), said reactive groups may be optionally protected with a suitably selected protecting groups, according to known methods. The protecting group is then removed, according to known methods, at a suitable subsequent step within the process. Conventional protecting groups, as well as methods of the attachment and removal of such groups are described in for example, T. W. Greene & P. G. M. Wuts, *Protective Groups in Organic Synthesis*, John Wiley & Sons, 1991, and similar standard texts.

When a particular group is "substituted" (e.g., alkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 60%, more preferably, the enantiomer is present at an enantiomeric excess of greater than or equal to about 75%, more preferably, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 60%, more preferably, the diastereomer is present at an diastereomeric excess of greater than or equal to about 75%, more preferably, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Furthermore, it is intended that within the scope of the present invention, any element, in particular when mentioned in relation to a compound of formula (I), shall comprise all isotopes and isotopic mixtures of said element, either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of formula (I) may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

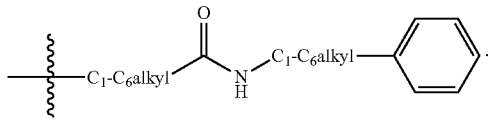

Abbreviations used in the specification, particularly the Schemes and Examples, are as follows:
AcN or MeCN=Acetonitrile
Alloc=Allyloxycarbonyl
Boc or BOC=tert-Butoxycarbonyl
CBz=Carboxybenzyl
Cinnoc=Cinnamyl Carbonate or Cinnamyl Oxycarbonyl
CMB=Calculated mass balance
DCM=Dichloromethane
DME=Dimethoxyethane
DMF=Dimethylformamide
DMS=Dimethylsulfide
DMSO=Dimethylsulfoxide
d.e.=Diastereomeric Excess
d.r.=Diastereomeric Ratio
DSC=Differential Scanning calorimetry
EtOAc=Ethyl acetate
EtOH=Ethanol
HPLC=High Performance Liquid Chromatography
iPrOH=Isopropyl Alcohol (or isopropanol)
LCMS=Liquid Chromatography Mass Spectrometry
Lys=Lysine
Me=Methyl
MeCN=Acetonitrile
MeOH=Methanol
2MeTHF or 2-MeTHF=2-Methyl-tetrahydrofuran
MTBE=Methyl t-butyl ether
n.d.=Not Detected
NMR=Nuclear magnetic Resonance
NQAD™=Nano Quantity Analyte Detector
—OMe=Methoxy
Pd/C=Palladium on Carbon (Catalyst)
RT or rt=Room temperature
THF=Tetrahydrofuran
TLC=Thin Layer Chromatography The S-selective and R-selective enzyme catalyst(s) which may be used in the process(es) of the present invention include, but are not limited to, a hydrolytic enzyme, also known as a hydrolases. Hydrolases are generally divided into several sub classes, such as proteases (also often called peptidases), lipases, esterases, acylases, amidases, etc. The classification is largely based on the type of natural reaction that is catalysed by the enzymes.

In an embodiment, wherein the process of the present invention is directed to the preparation of enantiomerically enriched lisdexamfetamine, the S-selective enzyme catalyst is a hydrolase, wherein the hydrolase is not a natural (not chemically modified) lipase.

In an embodiment of the present invention, the S-selective or R-selective enzyme catalyst is a hydrolase enzyme other than a natural (not chemically modified) lipase. In an embodiment of the present invention, the hydrolytic enzyme is selected from the group consisting of proteases, esterases, acylases and amidases. In another embodiment of the present invention, the hydrolytic enzyme is a protease.

In another embodiment of the present invention, the S-selective or R-selective enzyme catalyst is a hydrolase (other than natural lipase) which can catalyse the formation of an amide bond. More particularly, the S-selective enzyme catalyst is a hydrolase (other than natural lipase) which can catalyse formation of an amide bond; wherein the amide bond is formed in the S-stereo-configuration. Similarly, the R-selective enzyme catalyst is a hydrolase which can catalyse formation of an amide bond; wherein the amide bond is formed in the R-stereo-configuration.

In a preferred embodiment, the S-selective or R-selective enzyme catalyst is a suitably selected protease enzyme. Preferably, the suitably selected protease is a protease enzyme derived from a *Bacillus* species, more preferably a protease enzyme derived from *Bacillus licheniformis*.

For use in the processes of the present invention, the enzyme catalyst may be used in its native, soluble form or it may be chemically modified or stabilized, as would be recognized by those skilled in the art (for example, the enzyme may immobilized on a solid particle, crystallized, aggregated or cross-linked to form a solid).

In an embodiment of the present invention, the enzyme catalyst is immobilized on solid particles (also known as solid support or substrate). The enzyme catalyst may be immobilized on solid particles in a non-covalent manner (in such a case the enzyme is located on the carrier (e.g. adsorbed onto the solid carrier) but not covalently attached), or in a covalently bonded manner. The enzyme may also be immobilized on itself, for example in Cross-linked Enzyme Crystals (CLEC's) and Cross-linked Enzyme Aggregates (CLEA's). In an embodiment of the present invention, the enzyme catalyst is immobilized. In another embodiment of the present invention, the enzyme catalyst is immobilized on solid particles. In another embodiment of the present invention, the enzyme catalyst is immobilized on solid particles in a covalent manner. In another embodiment of the present invention, the enzyme catalyst is immobilized on solid particles in a non-covalent manner. In another embodiment of the present invention, the enzyme catalyst s immobilized on itself in a crystallized, aggregated or cross-linked manner.

The solid particles on which the enzyme catalyst may be immobilized include, but are not limited to (a) acrylic beads, and the like, (b) solid particles or beads made from a metacrylate resin, a polyacrylate resin, a polyacrylamide polymer, a vinyl polymer, an allyl polymer, and the like, (c) silica or aluminum oxide particles, and the like. In an embodiment of the present invention, the solid particles are acrylic beads.

In an embodiment of the present invention, the S-selective or R-selective enzyme (preferably, hydrolase; more preferably protease) is encapsulated in a polyvinyl matrix.

Wherein the enzyme catalyst is immobilized on a solid substrate (such as acrylic beads), the amount or concentration of the enzyme catalyst per unit of substrate may vary. One skilled in the art will recognize that as the loading (e.g. concentration) of enzyme catalyst decreases, the total amount of solid substrate which is needed to reach the desired enzyme catalyst load may increase or decrease; as does the amount of solid substrate which needs to be removed at the end of the reaction/process.

One skilled in the art will further recognize that wherein the enzyme catalyst is present in a self-aggregated or self-cross-linked form, the rate of reaction may be affected by the ability of the enzyme to dissociate and/or interact with the reagents.

The enzyme catalyst may be obtained from natural sources, or may be produced by a genetically modified organism (for example, produced using host microorganisms such as *E. coli*, and the like). The enzyme catalyst may alternatively be genetically engineered (e.g. via altered amino acid sequence) in order to improve the catalytic properties for a certain substrate combination, solvent or other reaction conditions, as would be recognized by those skilled in the art. In an embodiment of the present invention, the enzyme catalyst is obtained from natural sources.

The enzyme catalyst may also be a mixture, for example, a mixture of two or more, preferably two to three, more preferably two, independently selected enzymes; wherein each enzyme is individually immobilized or non-immobilized. For example, the mixture may be a mixture of a suitably selected amidase and a suitably selected protease, each of which is independently immobilized or non-immobilized.

Suitably examples of S-selective enzyme catalysts, wherein the S-selective enzyme catalyst is immobilized on dry acrylic beads, include, but are not limited to the following (available from for example, ALIGN CHEMICALS or CHIRALVISION).

| Product ID No. | Product Specification |
|---|---|
| ALC-T2-250 | Protease from *Bacillus* sp.(Subtilisin, Alcalase ™) covalently attached to dry acrylic beads Beadsize 250-400 micrometer. Activity: 400 ELU/g. (Alcalase liquid = 4000 ELU/ml) |
| SAV-T2-250 | Protease from *Bacillus* sp. (Subtilisin, Savinase ™) covalently attached to dry acrylic beads Beadsize 250-400 micrometer. Activity: 750 ELU/g. |
| P6-T2-250 | Protease from *Bacillus licheniformis* (Protex 6L ™) covalently attached to dry acrylic beads Beadsize 250-400 micrometer. Activity: 400 ELU/g. (Protex 6 liquid = 4000 ELU/ml) |
| P8-T2-250 | Protease from *Bacillus licheniformis* (Protex 8L ™) covalently attached to dry acrylic beads Beadsize 250-400 micrometer. Activity: 500 ELU/g |
| P40L-T2-150 | Protease from *Bacillus subtilis* (Protex 40L ™) covalently attached to dry acrylic beads Beadsize 150-300 micrometer. Activity: 400 ELU/g. |
| AUAL-T2-250 | Protease from *Bacillus subtilis* (Alkaline protease ™) covalently attached to dry acrylic beads Beadsize 250-400 micrometer. Activity: 175 ELU/g. |

One skilled in the art will further recognize that the enzyme catalysts of the present invention are S-selective or R-selective.

In an embodiment of the present invention, the S-selective enzyme catalyst promotes greater than about 60% selectivity for the S-enantiomer. In another embodiment of the present invention, the S-selective enzyme catalyst promotes greater than about 75% selectivity for the S-enantiomer. In another embodiment of the present invention, the S-selective enzyme catalyst promotes greater than about 80% selectivity for the S-enantiomer. In another embodiment of the present invention, the S-selective enzyme catalyst promotes greater than about 85% selectivity for the S-enantiomer. In another embodiment of the present invention, the S-selective enzyme catalyst promotes greater than about 90% selectivity for the S-enantiomer. In another embodiment of the present invention, the S-selective enzyme catalyst promotes greater than about 95% selectivity for the S-enantiomer.

In an embodiment of the present invention, the R-selective enzyme catalyst promotes greater than about 60% selectivity for the R-enantiomer. In another embodiment of the present invention, the R-selective enzyme catalyst promotes greater than about 75% selectivity for the R-enantiomer. In another embodiment of the present invention, the R-selective enzyme catalyst promotes greater than about 80% selectivity for the R-enantiomer. In another embodiment of the present invention, the R-selective enzyme catalyst promotes greater than about 85% selectivity for the R-enantiomer. In another embodiment of the present invention, the R-selective enzyme catalyst promotes greater than about 90% selectivity for the R-enantiomer. In another embodiment of the present invention, the R-selective enzyme catalyst promotes greater than about 95% selectivity for the R-enantiomer.

As used herein, unless otherwise noted, the term "isolated form" shall mean that the compound is present in a form which is separate from any solid mixture with another compound(s), solvent system or biological environment. In an embodiment of the present invention, the compounds prepared according to the process(es) of the present invention are present in an isolated form.

As used herein, unless otherwise noted, the term "substantially pure form" shall mean that the mole percent of impurities in the isolated compound is less than about 5 mole percent, preferably less than about 2 mole percent, more preferably, less than about 1 mole percent, more preferably, less than about 0.5 mole percent, more preferably, less than about 0.2 mole percent, more preferably, less than about 0.1 mole percent. In an embodiment of the present invention, the compounds prepared according to the process(es) of the present invention are present in a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 1 mole percent more preferably, less than about 0.5 mole percent, more preferably less than about 0.2 mole percent, more preferably, less than about 0.1 mole percent. In an embodiment of the present invention, the compounds prepared according to the process(es) of the present invention are present in a form which is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Wherein an amount or numeric value herein is expressed as "greater than about X %", said expression is intended to mean a range of from about X % to about 100%, or any amount or range therein.

Examples of suitable solvents, bases, reaction temperatures, and other reaction parameters and components are provided in the detailed description which follows herein. One skilled in the art will recognize that the listing of said examples is not intended, and should not be construed, as limiting in any way the invention set forth in the claims which follow thereafter.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or mixture of solvents (i.e. solvent system); or alternatively may be run in different solvents or mixture of solvents following a suitable solvent exchange, which may be completed according to known methods.

One skilled in the art will further recognize that the reaction or process step(s) as herein described (or claimed) are allowed to proceed for a sufficient period of time until the reaction is complete, as determined by any method known to one skilled in the art, for example, chromatography (e.g. HPLC). In this context a "completed reaction or process step" shall mean that the reaction mixture contains a significantly diminished amount of the starting material(s)/reagent(s) and a significantly increased amount of the desired product(s), as compared to the amounts of each present at the beginning of the reaction.

In an embodiment, the amount of starting material remaining in the reaction mixture upon completion of the reaction or process step is less than about 50 mole %, more preferably less than about 35 mole %, more preferably less than about 25 mole %, more preferably less than about 20 mole %, more preferably, less than about 15 mole %, more preferably less than about 10 mole %, more preferably less than about 5 mole %, more preferably less than about 2 mole %, more preferably less than about 1 mole %.

In another embodiment, the amount of any desired reaction product, present in the reaction mixture, upon completion of the reaction or process step is greater than about 50 mole %, more preferably greater than about 75 mole %, more preferably greater than about 80 mole %, more preferably, greater than about 85 mole %, more preferably greater than about 90 mole %, more preferably greater than about 95 mole %, more preferably greater than about 98 mole %, more preferably greater than about 99 mole %.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)]\times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha-obs]/[\alpha-max])\times 100.$$

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention is directed to a process for the preparation of diastereomerically enriched amphetamine derivatives, compounds of formula (X)

wherein $R^1$ is selected from the group consisting of phenyl and benzyl; wherein the phenyl or benzyl is optionally substituted with one to three substituents independently selected from the group consisting of $C_{1-4}$alkyl and $C_{1-4}$alkoxy;

$R^2$ is selected from the group consisting of $C_{1-5}$alkyl;

$R^3$ is selected from the group consisting of hydrogen and $C_{1-4}$alkyl;

$R^4$ is an amino acid radical;

or a pharmaceutically acceptable salt thereof, as outlined in Scheme 1, below.

Scheme 1

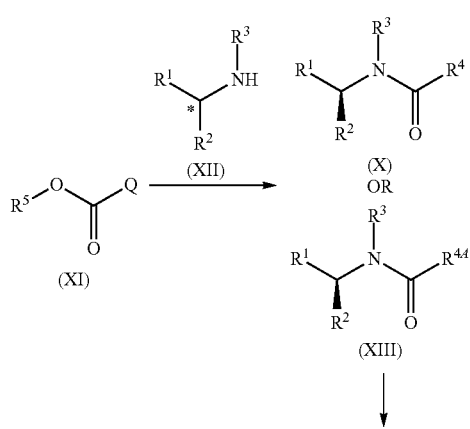

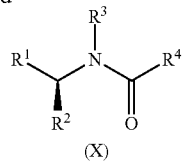

Accordingly, a suitably substituted compound of formula (XI), wherein Q is selected from the group consisting of $R^4$ (an amino acid radical) and $R^{4-4}$ (wherein $R^{4-4}$ is a nitrogen-protected amino acid radical), and wherein $R^5$ is selected from the group consisting of $C_{1-12}$alkyl, a known compound or compound prepared by known methods, is reacted with a suitably substituted compound of formula (XII), also known as amphetamine, also known as 1-phenylpropan-2-amine, a known compound or compound prepared by known methods: wherein the compound of formula (XII) is racemic or is present in an enantiomeric excess of one of its corresponding enantiomer (preferably its corresponding D-enantiomer), preferably, in an enantiomeric excess in the range of from about 1% to about 99%, or any amount or range therein, for example, in an enantiomeric excess of about 1%, 5%, 10%, 15%, 20%, 25%. 30%, 35%, 40%, 45%. 50%, 55%, 60%, 65%, 70%, 75%, 80%, 85%, 90%, 95%, 97%, 98%, 99% or 100%;

wherein the compound of formula (XII) is preferably present in an amount in the range of from about 1 to about 10 molar equivalents (relative to the moles of the compound of formula (XI)), or any amount or range therein, more preferably, in an amount in the range of from about 2 to about 7 molar equivalents, more preferably, in an amount in the range of from about 4 to about 6 molar equivalents, more preferably, in an amount of about 5 molar equivalents;

in the presence of a suitably selected S-selective enzyme catalyst, preferably a hydrolytic enzyme catalyst, more preferably a protease enzyme catalyst, more preferably a protease enzyme catalyst from a *Bacillus* species, more preferably a protease enzyme catalyst from *Bacillus licheniformis*, preferably an immobilized protease enzyme catalyst (from a *bacillus* species, preferably *Bacillus licheniformis*), for example, an immobilized protease enzyme catalyst selected from the group consisting of ALC-T2-250, SAV-T2-250, P6-T2-250, P8-T2-250, P40L-T2-150 and AUAL-T2-250 (commercially available from ChiralVision, Leiden, The Netherlands); preferably P6-T2-250, an immobilized protease enzyme catalyst of *Bacillus licheniformis* (commercially available as Protex 6L™);

wherein the protease enzyme catalyst (preferably, and enzyme catalyst immobilized on a solid support) is preferably present in an amount in the range of from about 1 wt % to about 500 wt % (relative to the amount (or weight) of the compound of formula (XI)), or any amount or range therein, more preferably, in an amount in the range of from about 10 wt % to about 200 wt %, more preferably, in an amount in the range of from about 50 wt % to about 200 wt %;

neat or in a suitably selected solvent or mixture of solvents (for example, in water, in an organic solvent or mixture of organic solvents or in an inorganic solvent or mixture of inorganic solvents, or in a mixture of water and suitably selected solvent), preferably in an organic solvent, more preferably in an organic solvent selected from the group consisting of tert-butyl-methylether (MTBE), tetrahydrofuran (THF), 2-methyl-tetrahydrofuran, 1,4-dioxane, acetonitrile, an alkyl alcohol (such as methanol, t-butanol, and the like), dimethylformamide (DMF), dimethylsulfide (DMS), toluene, dimethoxyethane (DME), and the like, and mixtures thereof; preferably acetonitrile, t-butanol or DME, more preferably acetonitrile, more preferably acetonitrile; wherein the solvent or mixture of solvents is preferably present in an amount in the range of from about 1:1 vol:vol ratio relative to the amount of the compound of formula (XI) to about 20:1 vol:vol ratio, more preferably in an amount in the range of from about 1:1 vol:vol ratio to about 15:1 vol:vol ratio, more preferably in an amount in the range of from about 2:1 vol:vol ratio to about 15:1 vol:vol ratio;

at a temperature in the range of from about 0° C. to about 120° C., or any temperature or range therein, preferably, at a temperature in the range of from about 20° C. to about 100° C., more preferably at a temperature in the range of from about 20° C. to about 80° C., more preferably, at a temperature in the range of from about 30° C. to about 70° C., for example, at a temperature in the range of from about 40° C. to about 60° C., for example, at a temperature in the range of from about 30° C. to about 45° C.; to yield the corresponding compound of formula (XIII).

One skilled in the art will recognize that in the process of the present invention, both the organic solvent or any of the mixtures as described above, and the amphetamine (the compound of formula (XII) act as the solvent for the reaction.

As used herein, unless otherwise noted, the compound of formula (XIa) shall mean the compound of formula (XI) wherein Q is $R^4$. The compound of formula (XIa) may therefore be represented by following structure:

(XIa)

As used herein, unless otherwise noted, the compound of formula (XIb) shall mean the compound of formula (XI) wherein Q is $R^{4A}$. The compound of formula (XIb) may therefore be represented by following structure:

(XIb)

One skilled in the art will recognize that wherein the compound of formula (XI), Q is $R^4$ (an amino acid radical), then the reaction of the compound of formula (XI) with the compound of formula (XII) yields the corresponding compound of formula (X).

One skilled in the art will further recognize that wherein the compound of formula (XI), Q is $R^{4A}$ (a nitrogen-protected amino acid radical), then the reaction of the compound of formula (XI) with the compound of formula (XII) yields the corresponding compound of formula (XIII). The compound of formula (XIII) is then de-protected, according to known methods, to yield the compound of formula (X). For example, wherein the nitrogen protecting group(s) is Boc or CBz, the compound of formula (XIII) may be de-protected by reacting with a suitably selected acid such as HCl, and the like (i.e. acid hydrolysis) or may be de-protected by reacting under hydrogenation conditions. In another example, wherein the nitrogen protecting group(s) is Alloc or Cinnoc, the compound of formula (XIII) may be de-protected by reacting with a suitably selected nucleophile such as 1,3-dimethylbarbituric acid, morpholine, and the like.

In an embodiment of the present invention, the compound of formula (XII) is racemic amphetamine. In an embodiment, the preferred ratio of racemic amphetamine (the compound of formula (XII)) to the compound of formula (XI) is in the range of from about 1/1 to about 10/1; or any ratio or range or ratios therein, preferably, the ratio is in the range of from about 2/1 to about 5/1, more preferably, the ratio is about 4/1.

In another embodiment of the present invention, the compound of formula (XII) is amphetamine enriched with its corresponding D-enantiomer (D-amphetamine. In another embodiment, the preferred ratio of the D-enantiomer enriched amphetamine/the compound of formula (XI) is in the range of from about 1/1 to about 10/1, or any ratio or range of ratios therein, preferably, the ratio is in the range of from about 2/1 to about 5/1, more preferably, the ratio is in the range of from about 3/1 about 4/1.

In another embodiment of the present invention, the compound of formula (XII) is amphetamine enriched with its corresponding L-enantiomer (L-amphetamine). In another embodiment, the preferred ratio of the D-enantiomer enriched amphetamine/the compound of formula (XI) is in the range of from about 1/1 to about 10/1, or any ratio or range of ratios therein, preferably, the ratio is in the range of from about 2/1 to about 5/1, more preferably, the ratio is in the range of from about 3/1 about 4/1.

One skilled in the art will recognize that in the process(es) of the present invention, the maximum possible (theoretical) yield of desired product will be limited by the amount of the corresponding desired enantiomer present in the compound of formula (XII). Thus, wherein the compound of formula (XII) is a racemate, the maximum possible (theoretical) yield of the desired compound of formula (X) is 50%. Wherein the compound of formula (XII) is enriched with its corresponding S-enantiomer, and the desired product is the corresponding S,S-diastereomer, then the maximum possible (theoretical) yield will greater than 50%, and is greater by the amount of S-enantiomer enrichment. Alternatively, wherein the compound of formula (XII) is enriched with its corresponding R-enantiomer, but the desired product is the corresponding S,S-diastereomer, then the maximum possible (theoretical) yield will be less than 50%, and is less by the amount of R-enantiomer enrichment.

In an embodiment of the present invention, the compound of formula (XIII) is isolated as a solid, preferably as a crystalline solid. In another embodiment of the present invention, the compound of formula (X) is isolated as a solid, preferably as a crystalline solid.

In an embodiment of the present invention, the compound of formula (XIII) is isolated under selective crystallization conditions, wherein the compound of formula (XIII) is isolated as a crystalline solid in an enantiomeric or diastereomeric excess of the desired stereoisomer of at least about 60%, preferably at least about 75%, more preferably at least about 80%, more preferably at least about 90%, more preferably, at least about 95%, more preferably at least about 97%, more preferably at least about 98%, more preferably, at least about 99%. In another embodiment of the present invention, the compound of formula (X) is isolated under selective crystallization conditions, wherein the compound of formula (X) is isolated as a crystalline solid in an enantiomeric or diastereomeric excess of the desired stereoisomer of at least about 60%, preferably at least about 75%, more preferably at least about 80%, more preferably at least about 90%, more preferably, at least about 95%, more preferably at least about 97%, more preferably at least about 98%, more preferably, at least about 99%.

In an embodiment of the present invention, the compound of formula (XIII) is isolated under selective crystallization conditions, wherein the compound of formula (XIII) is isolated as a crystalline solid in purity (as measured for example by HPLC) of at least about 60%, preferably at least about 75%, more preferably at least about 80%, more preferably at least about 90%, more preferably, at least about 95%, more preferably at least about 97%, more preferably at least about 98%, more preferably, at least about 99%. In another embodiment of the present invention, the compound of formula (X) is isolated under selective crystallization conditions, wherein the compound of formula (X) is isolated as a crystalline solid in purity (as measured for example by HPLC) of at least about 60%, preferably at least about 75%, more preferably at least about 80%, more preferably at least about 90%, more preferably, at least about 95%, more preferably at least about 97%, more preferably at least about 98%, more preferably, at least about 99%.

In an embodiment of the present invention, the compound of formula (XIII) is recrystallized according to known methods. In another embodiment of the present invention, the compound of formula (X) is recrystallized according to known methods.

The compound of formula (X) is further, optionally reacted with a suitably selected acid, to yield the corresponding acid addition salt, preferably the corresponding pharmaceutically acceptable acid addition salt.

One skilled in the art will recognize that the process as described in Scheme 1 above (and the text which follows therein) may alternative be adapted to yield a process for the preparation of a compound of formula (XX)

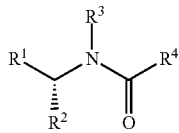

(XX)

or pharmaceutically acceptable salt thereof, by selecting and substituting a suitable R-selective enzyme catalyst for the S-selective enzyme catalyst.

The present invention is further directed to a process for the preparation of lisdexamfetamine, a compound of formula (I), as outlined in Scheme 2, below.

Scheme 2

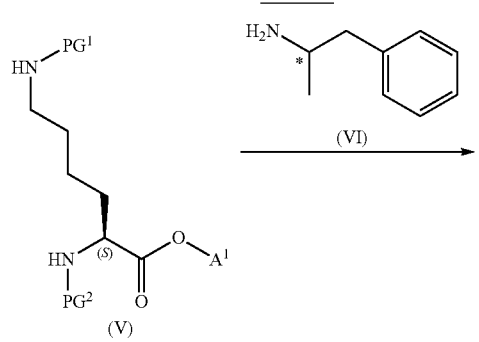

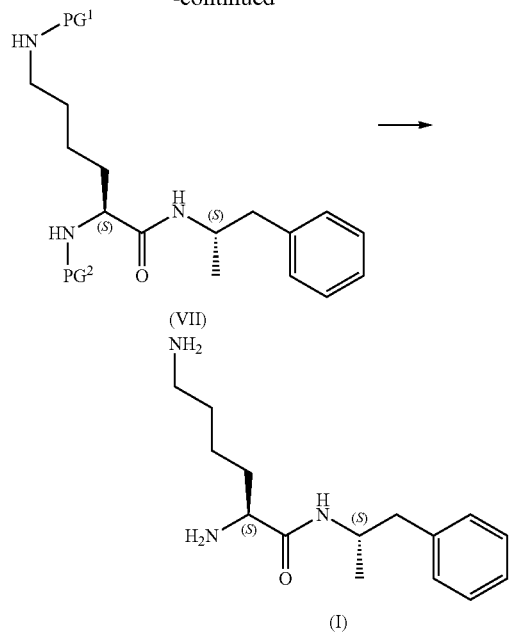

Accordingly, a suitably substituted compound of formula (V), wherein $PG^1$ is a suitably selected first nitrogen protecting group, wherein $PG^2$ is a suitably selected second nitrogen protecting group, preferably, $PG^1$ and $PG^2$ are independently selected from the group consisting of BOC, CBz, Alloc and Cinnoc, preferably, $PG^1$ and $PG^2$ are selected to be the same nitrogen protecting group, more preferably $PG^1$ and $PG^2$ are the same and are selected from the group consisting of Boc, CBz, Alloc and Cinnoc, more preferably, $PG^1$ and $PG^2$ are the same and are selected from the group consisting of Boc and CBz, and wherein $A^1$ is selected from the group consisting of $C_{1-5}$alkyl, preferably $C_{1-4}$alkyl, more preferably $C_{1-2}$alkyl, a known compound or compound prepared by known methods, is reacted with a suitably substituted compound of formula (VI), also known as amphetamine, also known as 1-phenylpropan-2-amine, a known compound or compound prepared by known methods: wherein the compound of formula (VI) is racemic or is present in an enantiomeric excess of one of its corresponding enantiomer (preferably its corresponding D-enantiomer), preferably, in an enantiomeric excess in the range of from about 1% to about 99%, or any amount or range therein, for example, in an enantiomeric excess of about 1%, 5%, 10%, 15%, 20%, 25%. 30%, 35%, 40%, 45%. 50%, 55%, 60%, 65%, 70%, 75%, 80%, 85%, 90%, 95%, 97%, 98%, 99% or 100%;

wherein the compound of formula (VI) is preferably present in an amount in the range of from about 1 to about 10 molar equivalents (relative to the moles of the compound of formula (V)), or any amount or range therein, more preferably, in an amount in the range of from about 2 to about 7 molar equivalents, more preferably, in an amount in the range of from about 4 to about 6 molar equivalents, more preferably, in an amount of about 5 molar equivalents;

in the presence of a suitably selected S-selective enzyme catalyst, preferably a hydrolytic enzyme catalyst, more preferably a protease enzyme catalyst, more preferably a protease enzyme catalyst from a *Bacillus* species, more preferably a protease enzyme catalyst from *Bacillus licheniformis*, preferably an immobilized protease enzyme catalyst (from a *bacillus* species, preferably *Bacillus licheniformis*), for example, an immobilized protease enzyme catalyst selected from the group consisting of ALC-T2-250, SAV-T2-250, P6-T2-250, P8-T2-250, P40L-T2-150 and AUAL-T2-250 (commercially available from ChiralVision, Leiden, The Netherlands); preferably P6-T2-250, an immobilized protease enzyme catalyst of *Bacillus licheniformis* (commercially available as Protex 6L™);

wherein the protease enzyme catalyst (preferably, and enzyme catalyst immobilized on a solid support) is preferably present in an amount in the range of from about 1 wt % to about 500 wt % (relative to the amount (or weight) of the compound of formula (XI)), or any amount or range therein, more preferably, in an amount in the range of from about 10 wt % to about 200 wt %, more preferably, in an amount in the range of from about 50 wt % to about 200 wt %;

neat or in a suitably selected solvent or mixture of solvents (for example, in water, in an organic solvent or mixture of organic solvents or in an inorganic solvent or mixture of inorganic solvents, or in a mixture of water and suitably selected solvent), preferably in an organic solvent, more preferably in an organic solvent selected from the group consisting of tert-butyl-methylether (MTBE), tetrahydrofuran (THF), 2-methyl-tetrahydrofuran, 1,4-dioxane, acetonitrile, an alkyl alcohol (such as methanol, t-butanol, and the like), dimethylformamide (DMF), dimethylsulfide (DMS), toluene, dimethoxyethane (DME), and the like, and mixtures thereof; preferably acetonitrile, t-butanol or DME, more preferably acetonitrile, more preferably acetonitrile; wherein the solvent or mixture of solvents is preferably present in an amount in the range of from about 1:1 vol:vol ratio relative to the amount of the compound of formula (XI) to about 20:1 vol:vol ratio, more preferably in an amount in the range of from about 1:1 vol:vol ratio to about 15:1 vol:vol ratio, more preferably in an amount in the range of from about 2:1 vol:vol ratio to about 15:1 vol:vol ratio;

at a temperature in the range of from about 0° C. to about 120° C., or any temperature or range therein, preferably, at a temperature in the range of from about 20° C. to about 100° C., more preferably at a temperature in the range of from about 20° C. to about 80° C., more preferably, at a temperature in the range of from about 30° C. to about 70° C., for example, at a temperature in the range of from about 40° C. to about 60° C., for example, at a temperature in the range of from about 30° C. to about 45° C.; to yield the corresponding compound of formula (VII).

In an embodiment of the present invention, the compound of formula (VI) is racemic amphetamine. In another embodiment, the preferred ratio of racemic amphetamine (the compound of formula (VI)) to the compound of formula (V) is in the range of from about 1/1 to about 10/1; preferably, the ratio is in the range of from about 2/1 to about 5/1, more preferably, the ratio is about 4/1.

In another embodiment of the present invention, the compound of formula (VI) is amphetamine enriched with its corresponding D-enantiomer (D-amphetamine). In another embodiment, the preferred ratio of the D-enantiomer enriched amphetamine/the compound of formula (V) is in the range of from about 1/1 to about 10/1, or any ratio or range of ratios therein, preferably, the ratio is in the range of from about 2/1 to about 5/1, more preferably, the ratio is in the range of from about 3/1 about 4/1.

In another embodiment of the present invention, the compound of formula (VI) is amphetamine enriched with its corresponding L-enantiomer (L-amphetamine). In another embodiment, the preferred ratio of the L-enantiomer enriched amphetamine/the compound of formula (V) is in the range of from about 1/1 to about 10/1, or any ratio or range of ratios therein, preferably, the ratio is in the range of from about 2/1 to about 5/1, more preferably, the ratio is in the range of from about 3/1 about 4/1.

In an embodiment of the present invention, enantiopure dexamphetamine (i.e. wherein the compound of formula (VI) is pure D-amphetamine or is present in an enantiomeric excess of its corresponding D-enantiomer of 100%) is reacted with the compound of formula (V), in the presence of the enzyme catalyst, according to the process as outlined in Scheme 2 above, and further as illustrated in Example 8, which follows hereinafter.

One skilled in the art will recognize that one advantage of the enzyme catalyzed process(es) of the present invention (for example, as described in Schemes 1-2 above, and in Example 8 which follows hereinafter) over traditional method(s) of preparing lisdexamfetamine (for example as described in BAUER, M. J. et al., US Patent Application Publication US 2012/0157706, assigned to CAMBREX) is that the product mixture resulting from the enzyme catalyzed process(es) of the present invention is free of N-hydroxysuccinimide impurity (where the N-hydroxysuccinimide impurity is known to be difficult to remove by crystallization), resulting in a product an improved impurities profile (fewer impurities and/or lower total % impurities).

One skilled in the art will further recognize that the enzyme catalyzed process(es) of the present invention are similarly advantageous over processes wherein lisdexamfetamine is prepared via peptide coupling. More particularly, the product mixture resulting from the enzyme catalyzed process(es) of the present invention are free of residual peptide coupling reagents and free of peptide coupling by-products, which by-products are often difficult to remove from the product lisdexamfetamine without loss of yield or additional purification steps.

Thus, an object of the present invention is a process for the preparation of lisdexamfetamine or pharmaceutically acceptable salt thereof (preferably lisdexamfetamine dimesylate), wherein the product prepared according to the process has an improved impurity profile (as compared with the process(es) known in the art).

In an embodiment of the present invention, the compound of formula (VII) is isolated as a solid, preferably as a crystalline solid. In one embodiment of the present invention, the compound of formula (VII) is isolated as an oil which is allowed to stand at room temperature, to yield a solid.

In another embodiment of the present invention, the compound of formula (VII) is isolated under selective crystallization conditions, wherein the compound of formula (VII) is isolated as a crystalline solid in a diastereomeric excess of the desired (S,S)-diastereomer at least about 60%, preferably at least about 75%, more preferably at least about 80%, more preferably at least about 90%, more preferably, at least about 95%, more preferably at least about 97%, more preferably at least about 98%, more preferably, at least about 99%.

In another embodiment of the present invention, the compound of formula (VII) is isolated under selective crystallization conditions, wherein the compound of formula (VII) is isolated as a crystalline solid in purity (as measured for example by HPLC) of at least about 60%, preferably at least about 75%, more preferably at least about 80%, more preferably at least about 90%, more preferably, at least about 95%, more preferably at least about 97%, more preferably at least about 98%, more preferably, at least about 99%.

In another embodiment of the present invention, the compound of formula (VII) is recrystallized according to known methods, from a suitably selected organic solvent or mixture of organic solvents, such as diethyl ether, a mixture of dichloromethane and diethyl ether, and the like. In another embodiment of the present invention, the compound of formula (VII) is recrystallized from warm diethyl ether to yield the (S,S)-diastereomer as a white solid.

The compound of formula (VII) is de-protected according to known methods, to yield the corresponding compound of formula (I). For example, the compound of formula (VII) may be de-protected by reacting with a suitably selected acid such as HCl, and the like (i.e. acid hydrolysis) or may be de-protected by reacting under hydrogenation conditions. In an embodiment of the present invention, the compound of formula (VII) is de-protected in the 1,4-dioxane and in the presence of methanesulfonic acid (wherein the methanesulfonic acid is present in an amount in the range of from about 2 to about 10 molar equivalents, preferably, in an amount in the range of from about 3 to about 7 molar equivalents, more preferably, in an amount in the range of from about 4 to about 6 molar equivalents, more preferably in an amount of about 5 molar equivalents); to yield the corresponding dimesylate salt of the compound of formula (I); wherein the dimesylate salt of the compound of formula (I) is preferably present in a diastereomeric excess (d.e.) greater than or equal to that of the d.e. of the compound of formula (VII), preferably, the d.e. of the compound of formula (I) is greater than the d.e. of the compound of formula (VII).

The compound of formula (I) is further, optionally reacted with a suitably selected acid, to yield the corresponding acid addition salt. In an embodiment, the compound of formula (I) is reacted with methanesulfonic acid; to yield the corresponding dimesylate salt of the compound of formula (I).

In certain embodiments, the present invention is directed to a process for the preparation of a compound of formula (VII), a compound of formula (I) or a pharmaceutically acceptable salt of the compound of formula (I) (preferably a dimesylate salt of the compound of formula (I)), wherein the desired compound is prepared with an overall yield in the range of from about 10% to about 95%, or any amount or range therein, preferably in the range of from about 25% to about 75%, or any amount or range therein.

In certain embodiments, the present invention is directed to a processes for the preparation of a compound of formula (VII), a compound of formula (I) or a pharmaceutically acceptable salt of the compound of formula (I) (preferably a dimesylate salt of the compound of formula (I)), wherein the desired compound is isolated as a solid in a diastereomeric excess of at least about 60%, preferably at least about 75%, more preferably at least about 80%, more preferably at least about 90%, more preferably, at least about 95%, more preferably at least about 97%, more preferably at least about 98%, more preferably, at least about 99%.

In certain embodiments, the present invention is directed to a processes for the preparation of a compound of formula (VII), a compound of formula (I) or a pharmaceutically acceptable salt of the compound of formula (I) (preferably a dimesylate salt of the compound of formula (I)), wherein the desired compound is isolated as a solid in purity (as measured for example by HPLC) of at least about 60%, preferably at least about 75%, more preferably at least about 80%, more preferably at least about 90%, more preferably, at least about 95%, more preferably at least about 97%, more preferably at least about 98%, more preferably, at least about 99%.

The present invention further comprises pharmaceutical compositions containing one or more compounds of formula (I) or compound of formula (X) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 1 mg to about 100 mg or any amount or range therein, and may be given at a dosage of from about 0.1 mg/kg/day to about 1.5 mg/kg/day, or any amount or range therein, preferably from about 0.1 mg/kg/day to about 1 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of, for example, attention deficit hyperactivity disorder is required.

The daily dosage of the products may be varied over a wide range from about 1 mg per day to about 100 mg per day. For oral administration, the compositions are preferably provided in the form of tablets containing, 1.0, 2.5, 5.0, 10.0, 15.0, 25.0, 30.0, 50.0 and 70.0 and 100, milligrams of the active ingredient for the symptomatic adjustment of the dosage to the patient to be treated. An effective amount of the drug is ordinarily supplied at a dosage level of from about 0.1 mg/kg to about 1.5 mg/kg of body weight per day, or any amount or range therein. Preferably, the range is from about 0.1 to about 1 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

EXAMPLES

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

Boc-L-Lys(Boc)-OH

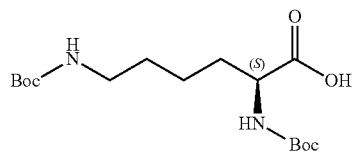

A 2 L three-neck flask equipped with a mechanical stirrer was charged with a solution of L-lysine monohydrochloride (50.03 g, 274 mmol) in water (275 ml), 1,4-dioxane (275 ml) and 1 M sodium hydroxide solution (275 mmol, 275 ml) (resulting: pH 10.0). To this solution was added di-tert-butyl dicarbonate (179 g, 820 mmol) in one portion whilst stirring. The evolution of gas was noted, and the pH of the reaction mixture slowly decreased. A Metrohm Titrino 702 SM dosing unit was set up in "Set Endpoint Titration" mode in order to keep the pH of the reaction mixture constant at pH 7.30 by automatically dosing 1 M NaOH. Note: the reaction mixture apparently formed a buffered system at pH 7.05.

LCMS (NQAD detection) indicated near-complete consumption of the lysine starting material after a reaction time of 20 h. The reaction mixture was concentrated by rotary evaporation to a total volume of ~500 mL. Water (250 mL) was added (resulting pH: 8.8) and then EtOAc was added (250 mL). Solid $KHSO_4$ (~70 g) was added in portions until a pH of 2.3 was reached (Note: evolution of gas; the mixture formed a buffer at pH 2.3). The phases were separated, the aqueous layer was extracted with EtOAc (2×250 mL) and the combined organic phases were washed sequentially with 0.25 M $KHSO_4$ (2×100 mL), water (50 mL) and brine (2×50 mL). Drying over $Na_2SO_4$ and concentration in vacuo yielded the title compound as a clear, colorless, sticky mass (98.18 g).

LCMS: Purity (NQAD detection): 99%, mass in agreement with molecular formula (neg. m/z=345 $[M-1]^-$, 691 $[2M-1]^-$).

TLC (EtOAc/heptane=1/1 containing 2 vol % AcOH, anisaldehyde staining): One major spot ($R_f$ 0.28), no $Boc_2O$ present. A small impurity with a higher $R_f$ was visible.

Kaiser test: negative (no primary amines present).

Isolated yield: 92%

Example 2

Boc-L-Lys(Boc)-OMe

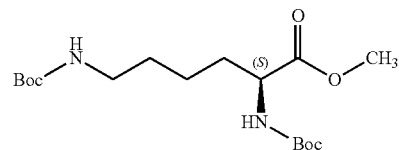

A 1 L three-neck flask equipped with addition funnel, nitrogen inlet, thermometer and mechanical stirrer was charged with a solution of Boc-L-Lys(Boc)-OH (59.37 g, 161 mmol, 94 wt % in EtOAc) in N,N-dimethylformamide (anhydrous) (300 mL). Whilst stirring, potassium carbonate (24.5 g, 177 mmol) was added, and the resulting suspension was cooled on an ice bath to an internal temperature of +10° C. Iodomethane (34.3 g, 242 mmol, 15.04 mL) was added dropwise over 30 min via the addition funnel, while keeping the internal temperature <20° C. The ice bath was removed and the reaction mixture was allowed to reach room temperature. TLC indicated complete consumption of the starting material after 4.5 h of stirring at room temperature. All volatiles were removed in vacuo, the resulting white slurry solidified on standing, and it was stored at −20° C. overnight. The resultant material was taken up in water (1 L) and sat'd. $NaHCO_3$ (0.5 L), and then extracted with EtOAc (3×500 mL). The combined organic phases were washed with dilute brine (2×200 mL), brine (2×100 mL), then dried over $Na_2SO_4$ and concentrated. After stripping with heptane (2×200 mL), the title compound was isolated as a white solid (57.08 g, 97% yield).

$^1$H-NMR ($CDCl_3$): In agreement with structure.

LCMS (NQAD detection): Purity >99%, mass in agreement with molecular formula (pos. m/z=361 $[M+1]^+$, 383 $[M+Na]^+$).

Specific rotation: $[\alpha]_D^{22}$=6.38° (c=1.72, $CHCl_3$).

TLC (EtOAc/heptane=1/1; ninhydrine staining): $R_f$ 0.54, a small impurity with a higher $R_f$ was present (carried over from the starting material).

Example 3

(S,S)-Bis-Boc-Lisdexamfetamine

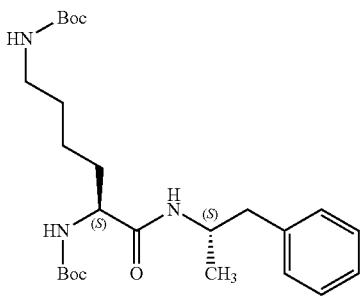

Inside a 100 mL three-neck flask equipped with a mechanical stirrer (teflon blade), a reflux condenser and a drying tube (CaCl$_2$), a solution of Boc-L-Lys(Boc)-OMe (prepared as in Example 2 above, 5.01 g, 13.90 mmol) in acetonitrile (10 mL) was prepared. The resultant mixture was heated to 40° C. and then 1-phenylpropan-2-amine (9.38 g, 69.4 mmol) was added, followed immediately by addition of the protease of *Bacillus licheniformis* on solid support (ChiralVision P6-T2-250) (2.5 g). The resultant mixture was stirred at 100 rpm at 40° C. for 68 h, after which time HPLC and LCMS indicated virtually complete consumption of the starting material. The reaction mixture was decanted with the aid of MeCN (3×50 mL) and the decanted liquids were passed through a paper filter. The volatiles of the filtrate were removed in vacuo resulting in a yellowish oil to which water (200 mL) and 1 M KHSO$_4$ (50 mL) were added (resulting in pH 2). The phases were separated and the aqueous layer was extracted with EtOAc (1×100 ml, 2×50 mL), and the combined organic phases were washed sequentially with water (50 mL), saturated NaHCO$_3$ solution (50 mL) and brine (50 mL). Drying over Na$_2$SO$_4$ and concentration in vacuo yielded an off-white solid. This material was applied on a silica column as a solution in CH$_2$Cl$_2$ (10 mL) and eluted with 10%→66% EtOAc in heptane. Appropriate fractions were collected and concentrated to yield the title compound as a white solid (4.62 g, 72% yield).

$^1$H-NMR (CDCl$_3$): In agreement with structure; contains 0.8% (w/w) heptane.

LCMS: Purity 98.7% (DAD 210 nm), mass in agreement with molecular formula (pos. m/z=464 [M+1]$^+$).

HPLC: Purity >99% (DAD 210 nm).

Chiral LC: Diastereomeric ratio: (S,S)/(S,R)=93/7 (determined using Method A as described in Example 19)

TLC (EtOAc/heptane=1/1; ninhydrine staining): R$_f$ 0.46, one single spot.

Example 4

Purification of bis-Boc-Lisdexamfetamine

Bis-Boc protected Lisdexamfetamine (prepared as in Example 3 above, 150 mg, 86% d.e.) was dissolved in diethyl ether (4 mL) at reflux to yield a clear solution, which was allowed to cool to room temperature over 2 hours while stirring. The resulting precipitate was collected by filtration to yield the (S,S)-diastereomer of bis-Boc-protected lisdexamfetamine as a white solid in 64% recovery (96 mg) and 99.2% d.e. (determined using Method C as described in example 19). DSC measurements showed that the bis-Boc-protected Lisdexamfetamine melted at around 103° C.

Example 5

Lisdexamfetamine dimesylate

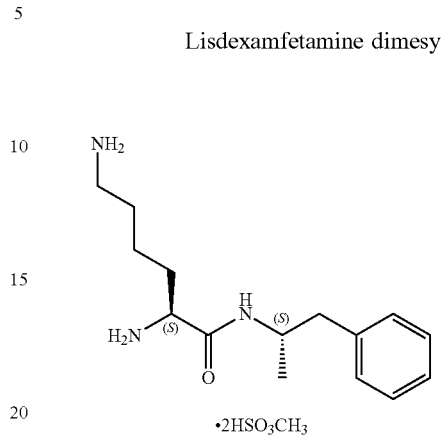

·2HSO$_3$CH$_3$

A 100 mL conical flask, equipped with a large magnetic stirring bar and fitted with a drying tube (CaCl$_2$), was charged with (S,S)-bis-Boc-lisdexamfetamine (prepared as in Example 3 or 4 above, 3.04 g, 6.56 mmol; d.r.=93/7) and 1,4-dioxane (dry) (22.5 mL). To the resulting, stirred solution was added dropwise methanesulfonic acid (2.13 mL, 32.8 mmol, 5 equiv). A slight exotherm was noted. The reaction mixture was stirred for 21 h at room temperature during which time it turned into a thick white slurry. The solids were collected by suction filtration over a P4 glass filter, the filter residue was washed with 1,4-dioxane (3×15 mL) and then dried under vacuum at 40° C. overnight to yield the title compound as a white solid (2.63 g, 87% yield).

$^1$H-NMR (dmso-d$_6$): In agreement with structure.

HPLC: Purity >99% (DAD 210 nm). Diastereomeric ratio: (S,S)/(S,R)=98.3/1.7 (determined using Method Gas described in Example 19)

LCMS: Purity >99% (DAD and NQAD, very broad peaks); mass in agreement with molecular formula of the free amine (pos. m/z=264 [M+1]$^+$).

Example 6

CBz-Lys(CBz)-OMe

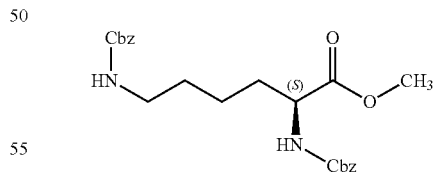

Bis-CBz protected L-Lysine (22.4 g) was treated with potassium carbonate (1.3 equiv.) and methyl iodide (1.8 equiv.) in DMF (100 mL). HPLC analyses showed that a virtually complete conversion was reached within 3 hours at room temperature. The reaction mixture was worked up by diluting with ice/water (500 mL) and then extracting with diethyl ether (3×250 mL). The organic layer was washed with water (2×300 mL) and brine (300 mL), then dried over Na$_2$SO$_4$ and concentrated to yield the title compound as a colorless oil (23.2 g, 97% yield).

HPLC: 97% purity (HPLC); >99% e.e. (determined using Method F as described in Example 19)

The ¹H-NMR and mass spectra were in agreement with the structure.

Example 7

Bis-CBz-protected Lisdexamfetamine

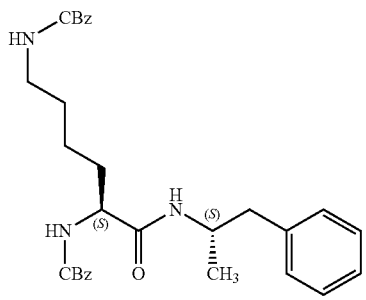

CBz-L-Lys(CBz)-OMe (prepared as in Example 6, above, 19.3 g) and rac-amphetamine (30.5 g, 5 equiv.) were dissolved in acetonitrile (300 mL). Immobilized protease of Bacillus licheniformis (10 g, ChiralVision, product code IMMP6-T2-250) was added (to suppress hydrolysis, the enzyme was first washed with dry acetonitrile (4×50 mL), prior to the addition of CBz-Lys(CBz)-OMe and amphetamine). The reaction mixture was stirred at 40° C. and monitored by HPLC. After 74 hours, HPLC analysis showed ca. 91% of the desired product and 2% starting material. Prolonging the reaction time did not lead to a full conversion of the starting material. The reaction was stopped and worked up by addition of DCM (0.9 L). The enzyme was removed by filtration to yield a clear solution. The filtrate was washed with 1M KHSO₄ (2×500 mL), and saturated aq. NaHCO₃ (500 mL), then dried and concentrated to yield the title compound as an off-white solid (22.1 g, 92% yield).

HPLC: 94% purity (HPLC), 89% d.e. (determined using Method C as described in Example 19.)

The isolated product was crystallized from methanol in three runs to yield bis-CBz-protected Lisdexamfetamine (14.6 g, 61% yield).

HPLC: 99.9% purity; 99.9% d.e. (Determined using Method C as described in Example 19)

DSC measurements showed that the isolated bis-CBz protected lisdexamfetamine melted at around 164° C.

Example 8

Bis-CBz-protected Lisdexamfetamine

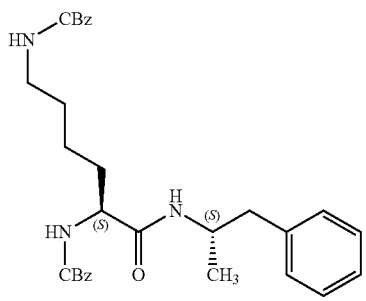

Dextroamphetamine tartrate salt (1.6 g, 5 equiv.) was treated with a NaOH solution and extracted with diethyl ether. The organic layer was dried and concentrated to yield the free-base of dextroamphetamine as a colorless oil. The free base was added to a solution of CBz-L-Lys(CBz)-OMe (0.5 g) and immobilized protease of Bacillus licheniformis (250 mg, ChiralVision product code IMMP6-T2-250) in acetonitrile (10 mL). The reaction mixture was stirred at 40° C. for 40 hours. The reaction mixture was diluted with DCM (20 mL) and filtrated using a phase separator to remove the enzyme. The filtrate was washed with 1M KHSO₄ (2×10 mL), and satd. aq. NaHCO₃ (10 mL), then dried over Na₂SO₄ and concentrated to yield CBz-protected lisdexamfetamine (0.38 g, 58% yield).

HPLC 95% purity and >99.9 d.e. (determined using Method C as described in Example 19)

One skilled in the art will recognize that one advantage of the enzyme catalyzed acylation with enantiopure dexamphetamine (as described in Example 8 above) over the traditional method of preparing Lisdexamfetamine is that the enzymeally prepared product is free of N-hydroxysuccinimide residue, which is very difficult to remove by crystallization, as described in BAUER, M. J. et al., US Patent Application Publication US 2012/0157706 A1.

Example 9

Lisdexamfetamine dimesylate

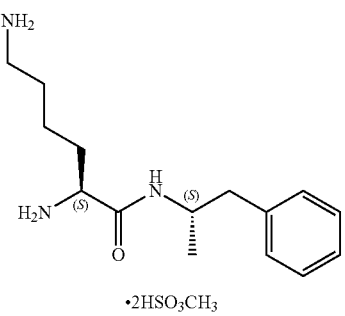

•2HSO₃CH₃

A 300 mL glass autoclave was charged with 10 g of bis-CBz-protected lisdexamfetamine and 1-butanol (100 mL). Pd/C (10 wt %, 0.25 g) was added and the reaction mixture was pressurized with hydrogen gas (5 bar) and heated to 85° C. After 18 hours, HPLC indicated complete conversion. The hot reaction mixture was filtered through a pad of CELITE and the filter cake washed with n-butanol (20 mL). The filtrate was concentrated to approximately 80 mL and methanesulfonic acid (0.76 g, 7.91 mmol, 0.514 mL) was slowly added at 40° C. After 30 min at 40° C. another portion of methanesulfonic acid (3.04 g, 31.6 mmol, 2.054 ml) was added over 30 minutes. The resultant wet suspension was stirred at 40° C. for 30 minutes after which time isopropyl acetate (50 mL) was added over 10 minutes. After another 30 minutes at 40° C. and 30 minutes at 15° C., the precipitate was collected by filtration and washed with a mixture of 1-butanol (15 mL) and isopropyl acetate (5 mL), and then washed with pure isopropyl acetate (20 mL). The wet cake was dried to yield lisdexamfetamine dimesylate as a white solid (7.2 g, 83% yield).

HPLC: 99.3% purity and >99.9% d.e. (determined using Method G as described in Example 19)

The ¹H-NMR was in agreement with the structure.

Example 10

Alloc-L-Lys(Alloc)-OMe

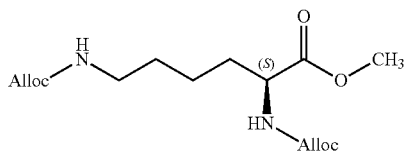

A solution of L-lysine methyl ester dihydrochloride (10.0 g) and potassium carbonate (30.0 g, 5 equiv.) in water (170 mL) at 0° C. was treated with allylchloroformate (9.6 mL, 2.1 equiv.). After 3 hours, the reaction mixture was extracted with diethyl ether. The organic layer was washed sequentially with 1M KHSO₄, saturated aq. NaHCO₃ and brine, then dried over Na₂SO₄ and concentrated. The resulting residue was purified by flash chromatography (heptane: ethyl acetate 1:1), to yield the title compound as a colorless oil. (10.7 g, 73% yield).

HPLC: 96% purity and >99% e.e. (determined using Method D as described in Example 19)

The ¹H-NMR was in agreement with the structure.

Example 11

Bis-Alloc-protected Lisdexamfetamine

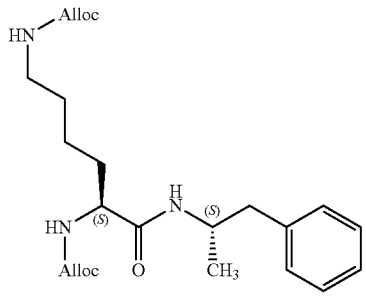

Alloc-L-Lys(Alloc)-OMe (prepared as in Example 10 above, 9.0 g) and rac-amphetamine (18.5 g, 5 equiv.) were dissolved in acetonitrile (140 mL) and immobilized protease of *Bacillus licheniformis* (4.5 g, ChiralVision, product code IMMP6-T2-250) was added. (To suppress possible hydrolysis of the methyl ester, the enzyme was first washed with dry acetonitrile (4×50 mL)). The reaction mixture was stirred at 40° C. and the progress was monitored by TLC (heptane: ethyl acetate 1:1, KMnO₄ visualization). After 70 hours (over weekend) TLC indicated complete conversion. The reaction was worked up by addition of DCM (500 mL) and the enzyme was filtered off to yield a clear solution. (A sample of the filtrate (2 mL) was washed with 3N HCl, filtered over a phase-separator and evaporated. HPLC analysis showed 94% purity and 88% d.e.). The filtrate was evaporated to dryness and triturated with diethyl ether (200 mL). The resulting precipitate was collected and washed with diethyl ether (50 mL) to yield bis-Alloc-protected lisdexamfetamine as a white solid. (10.4 g, 88% yield).

HPLC: 97% purity and 96% d.e. (Determined using Method C as described in Example 19.)

Crystallization from a mixture of DCM and diethyl ether (3:10, ca 250 mL) yielded bis-Alloc-Lisdexamfetamine (9.5 g, 80% recovery) and 98.4% d.e. This product was triturated with diethyl ether several times to yield bis-Alloc-protected Lisdexamfetamine (7.9 g, 67% recovery).

HPLC: 98% purity and 99% d.e. (determined using Method C as described in Example 19.)

DSC measurements showed that the isolated bis-Alloc protected Lisdexamfetamine melted at around 151° C.

Example 12

Lisdexamfetamine dimesylate

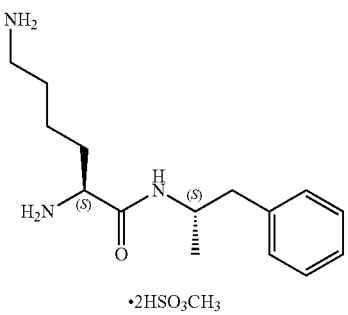

Bis-Alloc-protected Lisdexamfetamine (prepared as in Example 11 above, 7.4 g) was dissolved in THF (150 mL) and treated with tetrakis(triphenylphosphine)palladium(0) (198 mg, 1% (mol/mol)) and morpholine (6 mL, 4 equiv.). The reaction mixture was stirred at room temperature and monitored by HPLC. After 1 hour, the initially clear yellow solution had turned into a thick yellow mixture and HPLC showed complete conversion. The reaction mixture was diluted with MTBE (200 mL) and extracted with 2N HCl (2×100 mL). The water layer was made basic (pH=10) with 4N NaOH and then extracted with DCM (2×100 mL) (the organic layer contained only a trace of the desired product). The pH of the water layer was raised (pH=12) with K₂CO₃ (solid) and then extracted with THF (2×100 mL) (THF layer contained only a trace of product). The water layer was evaporated to dryness, acetonitrile (300 mL) was added to the residue and the resultant mixture was stirred at 40° C. for 30 min. The solid was filtered off and the acetonitrile was evaporated to yield (S,S)-lisdexamfetamine freebase as a light yellowish oil. ¹H-NMR showed the expected signals for Lisdexamfetamine and a trace of solvents and morpholine. The volatiles were removed by rotary evaporation to yield (S,S)-lisdexamfetamine freebase (3.1 g, 67% yield) as a light yellowish solid.

HPLC: 98% purity and >99% d.e. (determined using Method G as described in Example 19)

Methanesulfonic acid (0.30 mL, 0.41 equiv.) was added to a solution of (S,S)-lisdexamfetamine freebase (3.0 g, prepared as described above) in n-butanol (48 mL) at 40° C. After 30 minutes at 40° C., another portion of methanesulfonic acid (1.19 ml, 1.61 equiv.) was added over 30 minutes. The resulting suspension was stirred at 40° C. for 30 minutes after which time isopropyl acetate (30 mL) was added over 10 minutes. After another 30 minutes at 40° C. and then 30 minutes at 15° C., the precipitate was collected by filtration and washed with a mixture of 1-butanol (10 mL) and isopropyl acetate (6 ml) and then with pure isopropyl acetate (15 mL). The wet filter cake was dried to yield lisdexamfetamine dimesylate as a white solid. (4.97 g, 95% yield).

HPLC: 99% purity.

The $^1$H-NMR was in agreement with the structure and the HPLC showed only 0.02% of the undesired (S,R) diastereomer.

Example 13

Cinnoc-L-Lys(Cinnoc)-OCH$_3$

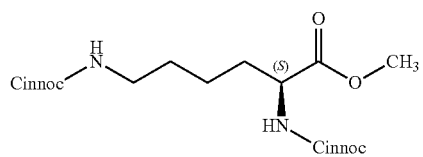

A solution of cinnamyl alcohol (17.6 g, 3.4 equiv.) in THF (100 mL) was added drop-wise under a nitrogen atmosphere to a solution of triphosgene (13.1 g, 1.15 equiv.) in THF (200 mL) at −5° C., followed by addition of triethylamine (18.2 mL, 3.4 equiv.). The resulting suspension was stirred at −5° C. for 1 hour and TLC (silica, heptane:ethyl acetate 1:1) showed a complete conversion of the alcohol. The reaction mixture was then filtered under nitrogen atmosphere and immediately added drop-wise (over 90 min) to a solution of L-lysine methyl ester dihydrochloride (9 g, 1 equiv.) and K$_2$CO$_3$ (32 g, 6 equiv.) in water (200 mL) at 0° C. After the mixture was stirred for 10 minutes, the cooling medium was removed and stirring was continued for 18 hours during which time the reaction mixture was allowed to come to room temperature. The THF layer was separated and the water layer was extracted with diethyl ether (2×100 mL). The combined organic layers were washed with 1N HCl (2×100 mL), brine (100 mL), dried and evaporated to yield Cinnoc-L-Lys(Cinnoc)-OMe as a residue. The resulting material was purified by flash chromatography (silica, 20-40% ethyl acetate in heptane) to yield Cinnoc-L-Lys(Cinnoc)-OMe as a white solid (5.0 g, 26% yield)

HPLC: 97% purity and >99.9% e.e. (determined using Method E as described in Example 19)

Example 14

Bis-Cinnoc-Lisdexamfetamine

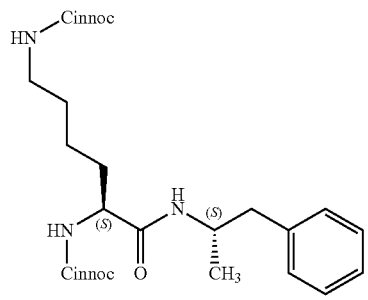

Cinnoc-L-Lys(Cinnoc)-OMe (prepared as in Example 13, above, 4.9 g) and rac-amphetamine (7.0 g, 5 equiv.) were dissolved in acetonitrile (80 mL) and immobilized protease of *Bacillus licheniformis* (2.5 g, ChiralVision, product code IMMP6-T2-250) was added (in order to suppress hydrolysis, the enzyme was first washed with dry acetonitrile (4×30 mL), prior to the addition to Cinnoc-L-Lys(Cinnoc)-OMe). The reaction mixture was stirred at 40° C. and monitored by HPLC. After 110 hours, HPLC analysis showed ca. 87% of the desired product and 8% starting material. A chiral HPLC analysis of the reaction mixture showed ca. 92% d.e. for the product. The formed precipitate was collected by filtration, taken up in DCM (400 mL) and the remaining solid (enzyme) was removed by filtration. The volatiles were evaporated to yield bis-Cinnoc-lisdexamfetamine as a residue (5.8 g, 96% yield, not corrected for purity).

HPLC: 74% purity and 97% d.e. (determined using Method B as described in Example 19)

The residue was crystallized from DCM/acetonitrile in two runs to yield bis-Cinnoc-protected lisdexamfetamine as a white solid (3.6 g, 60% isolated yield)

HPLC: 99.9% purity and >99.9% d.e. (determined using Method B as described in Example 19)

DSC measurements showed that the isolated bis-Cinnoc-protected lisdexamfetamine melted at around 180° C.

Example 15

Lisdexamfetamine dimesylate

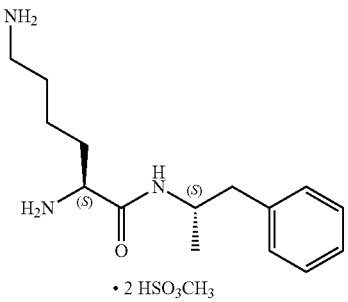

Bis-Cinnoc-protected lisdexamfetamine (prepared as in Example 14 above, 3.5 g) was treated with 1% mol/mol (69 mg) tetrakis(triphenylphosphine) palladium(0) and 1,3-dimethylbarbituric acid (2 g, 2.2 equiv.) in DCM (150 mL). The reaction was performed in a glovebox under an inert atmosphere to prevent de-activation of the catalyst. After 1 hour at room temperature, HPLC analysis showed a complete conversion. The reaction mixture was concentrated to dryness, and the residue was dissolved in 1-butanol (25 mL). Methanesulfonic acid (187 µL, 0.48 equiv.) was added and the mixture was stirred at 40° C. for 30 min. Another portion of methanesulfonic acid (631 µL, 1.62 equiv.) was added and the formed suspension was stirred at 40° C. for 30 minutes after which time isopropyl acetate (20 mL) was added. After another 30 minutes at 40° C. and then 30 minutes at 15° C., the precipitate was collected by filtration and washed with a mixture of 1-butanol (5 mL) and isopropyl acetate (5 ml) and then with pure isopropyl acetate (20 mL). The solid was dried to yield the title compound (2.6 g) in 97% purity (HPLC) as an off-white solid. The off-white solid was recrystallized from a mixture of methanol (8 mL) and acetonitrile (20 mL) to yield lisdexamfetamine dimesylate as a white solid (1.8 g, 65% yield).

HPLC: 99.3% purity and >99.9 d.e. (determined using Method G as described in Example 19)

Example 16

Effect of Solvent and Amount of Racemic Amphetamine Ratio

The effects of the selected solvent and the molar equivalents of racemic amphetamine on the coupling reaction for preparation of bis-Boc-lisdexamfetamine were investigated through a series of screening experiments.

Screw cap vials (8 mL) equipped with magnetic stirring bars were charged each with Boc-L-Lys(Boc)-OMe (prepared as in Example 2 above, 100 mg), the indicated quantity of racemic amphetamine, internal standard (veratrole) and the indicated solvent (1.5 mL). To each of the resulting solutions was added the immobilized protease of *B. licheniformis* (100 mg, P6-T2-250, ChiralVision). The vials were inserted into preheated reaction blocks at 40° C. and their contents were stirred at 750 rpm for 4.5 days.

Conversion rates were determined relative to the internal standard (veratrole) by HPLC. Chiral HPLC analysis was used to determine the diastereomeric ratio.

The conditions and results for the screening experiments were as shown in Table 1, below.

TABLE 1

Details of Solvent Screening Experiments

| Solvent | Rac-A[a] (Equiv.) | Time [days] | Conversion (%) Boc-L-Lys(Boc)-OCH$_3$ | Conversion (%) Amphetamine | Yield [%] | Diastereomeric ratio[b] (S,S)/(S,R) |
|---|---|---|---|---|---|---|
| THF | 2 | 4.5 | 28.2 | 20.2 | 22.8 | 99/1 |
| DME | 2 | 4.5 | 26.5 | 18.7 | 21.0 | >99/0 |
| MeCN | 2 | 4.5 | 66.0 | 42.0 | 56.4 | 96/4 |
| THF | 4 | 4.5 | 40.3 | 14.7 | 32.6 | >99/0 |
| DME | 4 | 4.5 | 36.6 | 13.4 | 30.9 | >99/0 |
| MeCN | 4 | 4.5 | 79.7 | 29.9 | 69.1 | 95/5 |
| THF | 10 | 4.5 | 52.9 | 10.9 | 44.7 | >99/0 |
| DME | 10 | 4.5 | 54.5 | 12.3 | 44.0 | >99/0 |
| MeCN | 10 | 4.5 | 81.2 | 15.5 | 71.4 | 96/4 |

[a]Rac-A = Racemic amphetamine (equivalents)
[b]The diastereomeric ratio was determined using the analytical Method A, as described in Example 19, which follows hereinafter.

Example 17

Effect of Solvent and Choice of Immobilized Protease

The effect of choice of immobilized protease on the coupling reaction for preparation of bis-Boc-lisdexamfetamine was investigated through a series of screening experiments.

Screw cap vials (8 mL) were charged each with Boc-L-Lys(Boc)-OMe (prepared for Example as in Example 2 above, 100 mg), rac-amphetamine (3 equiv), internal standard (veratrole) and the indicated solvent (1.5 mL). To each of the resulting solutions was added the indicated immobilized protease (100 mg, ChiralVision). The vials were inserted into preheated reaction blocks at 40° C. and their contents were shaken at 400 rpm and analyzed after 65 h.

Conversion rates were determined relative to the internal standard (veratrole) by HPLC, Chiral HPLC analysis was used to determine diastereomeric ratio.

The conditions and results for the screening experiments were as shown in Table 2, below. All results were measured following a reaction time of 65 hours.

TABLE 2

Screening of Immobilized Proteases, Solvents

| Enzyme type | Solvent | Conversion Boc-L-Lys(Boc)-OMe | Yield [%] | Diastereomeric ratio[c] (S, S)/(S, R) |
|---|---|---|---|---|
| ALC-T2-250 | MeCN | 63 | 58.2 | 95/5 |
|  | 2-MeTHF | 11.6 | 13.9 | >99/1 |
| SAV-T2-250 | MeCN | 50 | 38.8 | 3/7 |
|  | 2-MeTHF | 25.1 | 16.9 | 97/3 |
| EVE-T2-250 | MeCN | 20 | 18.1 | 96/4 |
|  | 2-MeTHF | 2.6 | 5.2 | n.d. |
| ESP-T2-250 | MeCN | 13 | 12.1 | 95/5 |
|  | 2-MeTHF | −0.2 | 2 | n.d. |
| P6-T2-250 | MeCN | 73 | 67.0 | 92/8 |
|  | 2-MeTHF | 18.0 | 19.0 | >99/1 |
| P7-T2-150 | MeCN | 11 | 7.7 | n.d. |
|  | 2-MeTHF | −1.1 | 1 | n.d. |
| P8-T2-250 | MeCN | 80 | 62.4 | 94/6 |
|  | 2-MeTHF | 73.9 | 42.0 | 98/2 |
| P30-T2-150 | MeCN | 49 | 40.8 | 95/5 |
|  | 2-MeTHF | 0.5 | 2.3 | n.d. |
| P40L-T2-150 | MeCN | 57 | 41.9 | 94/6 |
|  | 2MeTHF | 21.9 | 13.6 | 95/5 |
| P89-T2-250 | MeCN | 43 | 39.0 | 5/5 |
|  | 2-MeTHF | −1.0 | 1.2 | n.d. |
| AUAL-T2-250 | MeCN | 44 | 35.3 | 93/7 |
|  | 2-MeTHF | 21.7 | 16.2 | 97/3 |

[c]The diastereomeric ratio was determined using the analytical Method A, described in Example 19, which follows hereinafter.

Example 18

HPLC Method for Determining Conversion Rates and/or Product Purity

Samples of material prepared according to the Examples provided above were tested for conversion rate and/or purity of the desired product according to one of the following HPLC method.
Sample preparation: An appropriate amount of reaction mixture was dissolved in a 1:1 mixture of MeCN and MeOH.
  Column: Agilent XDB C18 5μ 4.6×150 mm
  Column temp: 35° C.
  Flow: 1.5 mL/min
  Eluent A: 0.1% phosphoric acid in water
  Eluent B: 0.1% phosphoric acid in acetonitrile
  Gradient: t=0 min 10% B
    t=1 min 10% B
    t=18 min 95% B
    t=23 min 95% B
  Run length: 23 min
  Detection: DAD (220-320 nm), (206-214 nm)

Example 19

Methods for Determining Diastereomeric Excess of Isolated Product

Samples of material prepared according to the Examples provided above were tested for the diastereomeric excess of the desired product according to one of the following eight HPLC methods.
Method A:
Sample preparation: An appropriate amount of the analyte (sample) was dissolved in a 1:1 mixture of MTBE and MeCN
  Column: Chiralpak IC (250 mm×4.6 mm 5μ)
  Flow: 1 ml/min Column temp: 35° C.
Eluent: MTBE/MeCN 98/2 (isocratic)
Run length: 30 min
Detection: DAD (220-320 nm, 220 nm and 210 nm)
Method B:
Sample preparation: An appropriate amount of the analyte (sample) was dissolved in EtOH.
Column: Chiralpak IC (250×4.6 mm 5µ)
Flow: 1 ml/min
Column Temp: 35° C.
Eluent: Heptane/ethanol 85/15 (isocratic)
Run length: 30 min
Detection: DAD (220-320 nm, 220 nm and 210 nm)
Method C:
Sample preparation: An appropriate amount of the analyte (sample) was dissolved in iPrOH.
Column: Chiralcel AD-H (250×4.6 mm 5µ),
Flow: 1 ml/min
Column Temp: 35° C.
Eluent: Heptane/isopropyl alcohol 80/20 (isocratic)
Run length: 30 min
Detection: DAD (220-320 nm, 220 nm and 210 nm)
Method D:
Sample preparation: An appropriate amount of the analyte (sample) was dissolved in iPrOH.
Column: Chiralcel AD-H (250×4.6 mm 5µ),
Flow: 1 ml/min
Column Temp: 35° C.
Eluent: Heptane/isopropyl alcohol 90/10 (isocratic)
Run length: 30 min
Detection: DAD (220-320 nm, 220 nm and 210 nm)
Method E:
Sample preparation: An appropriate amount of the analyte (sample) was dissolved in EtOH.
Column: Chiralpak IC (250×4.6 mm 5µ)
Flow: 1 ml/min
Column Temp: 35° C.
Eluent: Heptane/ethanol 80/20 (isocratic)
Run length: 30 min
Detection: DAD (220-320 nm, 220 nm and 210 nm)
Method F:
Sample preparation: An appropriate amount of the analyte (sample) was dissolved in iPrOH.
Column: Chiralcel AD-H (250×4.6 mm 5µ),
Flow: 1 ml/min
Column Temp: 35° C.
Eluent: Heptane/isopropyl alcohol 70/30 (isocratic)
Run length: 30 min
Detection: DAD (220-320 nm, 220 nm and 210 nm)
Method G
Sample preparation: An appropriate amount of reaction mixture was dissolved in a 1:1 mixture of MeCN and MeOH.
Column: Agilent XDB C18 5µ 4.6×150 mm
Flow: 1.5 ml/min
Column temp: 35° C.
Eluent A: 0.1% phosphoric acid in water
Eluent B: 0.1% phosphoric acid in acetonitrile
Gradient: t=0 min 2% B
t=1 min 2% B
t=18 min 95% B
t=23 min 95% B
Run length: 23 min
Detection: DAD (220-320 nm), (206-214 nm)

Formulation Example 1

Solid, Oral Dosage Form—Prophetic Example

As a specific embodiment of an oral composition, 100 mg of the compound prepared as in Example 5 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of a compound of formula (I)

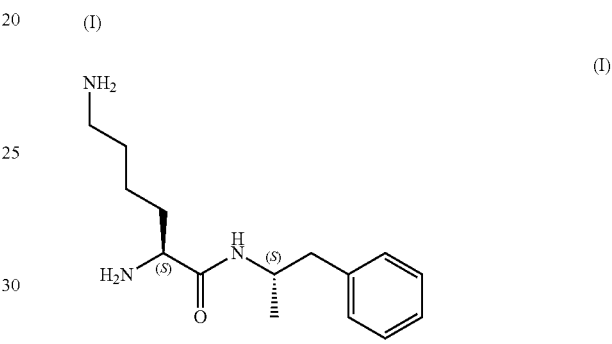

or a pharmaceutically acceptable salt thereof; comprising the steps of

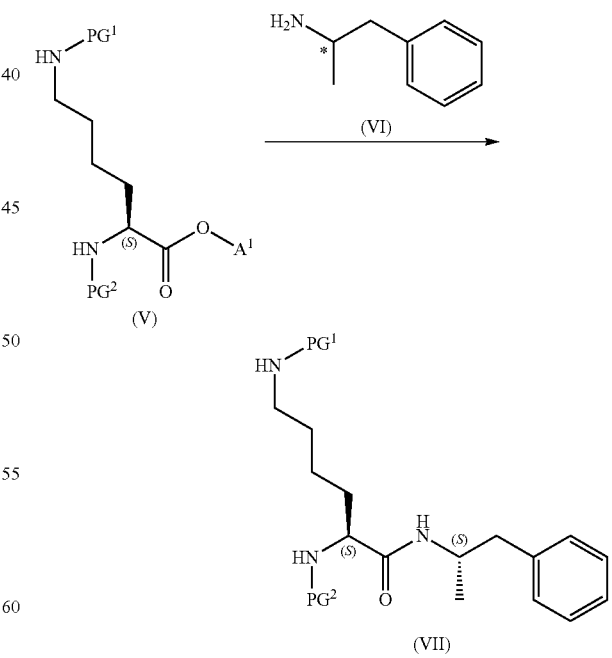

reacting a compound of formula (V), wherein
$PG^1$ and $PG^2$ are each tert-butoxycarbonyl (BOC), wherein $A^1$ is selected from the group consisting of $C_{1-12}$ alkyl, with a compound of formula (VI); wherein the compound of formula (VI) is racemic; in the presence of an S-selective enzyme catalyst; wherein the S-selective enzyme catalyst is an immobilized S-selective protease enzyme derived from *Bacillus lichenformis*; neat or in a solvent or in a mixture of solvents; to yield the corresponding compound of formula (VII); wherein the compound of formula (VII) is present in an enantiomeric excess;

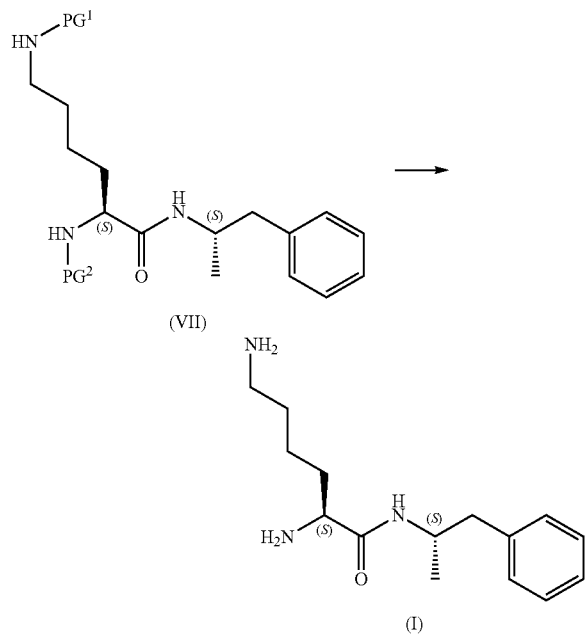

de-protecting the compound of formula (VII), to yield the corresponding compound of formula (I); wherein the compound of form6ula (I) is present in a diastereomeric excess.

2. A process as in claim 1, wherein $A^1$ is selected from the group consisting of methyl, ethyl, isopropyl and t-butyl.

3. A process as in claim 1, wherein $A^1$ is methyl.

4. A process as in claim 1, wherein the compound of formula (VI) is present in an amount in the range of from about 1 to 10 molar equivalents, relative to the moles of the compound of formula (V).

5. A process as in claim 1, wherein the compound of formula (VI) is present in an amount in the range of from about 4 to 6 molar equivalents, relative to the moles of the compound of formula (V).

6. A process as in claim 1, wherein the compound of formula (VI) is present in an amount of about 5 molar equivalents, relative to the moles of the compound of formula (V).

7. A process as in claim 1, wherein the S-selective enzyme catalyst is selected from the group consisting of P6-T2-250, and P8-T2-250.

8. A process as in claim 1, wherein the S-selective enzyme catalyst is P6-T2-250.

9. A process as in claim 1, wherein the protease enzyme catalyst is present in an amount in the range of from about 1 wt % to about 200 wt %.

10. A process as in claim 1, wherein the protease enzyme catalyst is present in an amount in the range of from about 50 wt % to about 200 wt %.

11. A process as in claim 1, wherein the compound of formula (V) is reacted with the compound of formula (VI) in a solvent; and wherein the solvent is an organic solvent.

12. A process as in claim 1, wherein the compound of formula (V) is reacted with the compound of formula (VI) in a solvent; wherein the solvent is an organic solvent; and wherein the organic solvent is selected from the group consisting of tert-butyl-methylether, tetrahydrofuran, 2-methyl-tetrahydrofuran, 1,4-dioxane, acetonitrile, methanol, t-butanol, dimethylformamide (DMF), dimethylsulfide (DMS), toluene, dimethoxyethane (DME) and mixtures thereof.

13. A process as in claim 1, wherein the compound of formula (V) is reacted with the compound of formula (VI) in a solvent; wherein the solvent is an organic solvent; and wherein the organic solvent is acetonitrile.

14. A process as in claim 1, wherein the compound of formula (V) is reacted with the compound of formula (VI) in a solvent; wherein the solvent is an organic solvent; wherein the organic solvent is acetonitrile and wherein the acetonitrile is present in an amount in the range of from about 1:1 vol:vol ratio relative to the amount of the compound of formula (VI) to about 20:1 vol:vol ratio.

15. A process as in claim 1, wherein the compound of formula (V) is reacted with the compound of formula (VI) in a solvent; wherein the solvent is an organic solvent; wherein the organic solvent is acetonitrile and wherein the acetonitrile is present in an amount in the range of from about 2:1 vol:vol ratio to about 15:1 vol:vol ratio, relative to the amount of the compound of formula (VI).

16. A process as in claim 1, wherein the compound of formula (V) is reacted with the compound of formula (VI) at a temperature in the range of from about 0° C. to about 120° C.

17. A process as in claim 1, wherein the compound of formula (V) is reacted with the compound of formula (VI) at a temperature in the range of from about 30° C. to about 70° C.

18. A process as in claim 1, wherein the compound of formula (V) is reacted with the compound of formula (VI) at a temperature in the range of from about 30° C. to about 45° C.

19. A process as in claim 1, wherein the ratio of the compound of formula (VI) to the compound of formula (V) is in the range of from about 3:1 to about 4:1.

20. A process as in claim 1, further comprising reacting the compound of formula (I) with methanesulfonic acid; to yield the corresponding dimesylate salt of the compound of formula (I).

21. A process as in claim 1, wherein the compound of formula (VII) is prepared in a diastereomeric excess of at least about 80%.

22. A process as in claim 1, wherein the compound of formula (I) is prepared in a diastereomeric excess of at least about 90%.

23. A process as in claim 1, wherein the compound of formula (I) is prepared in diastereomeric ratio of (S,S) to (S,R) diastereomers of about 98:2.

24. A process as in claim 1, wherein the dimesylate salt of the compound of formula (I) is prepared in a diastereomeric excess of at least about 80%.

25. A process for the preparation of a compound of formula (I)

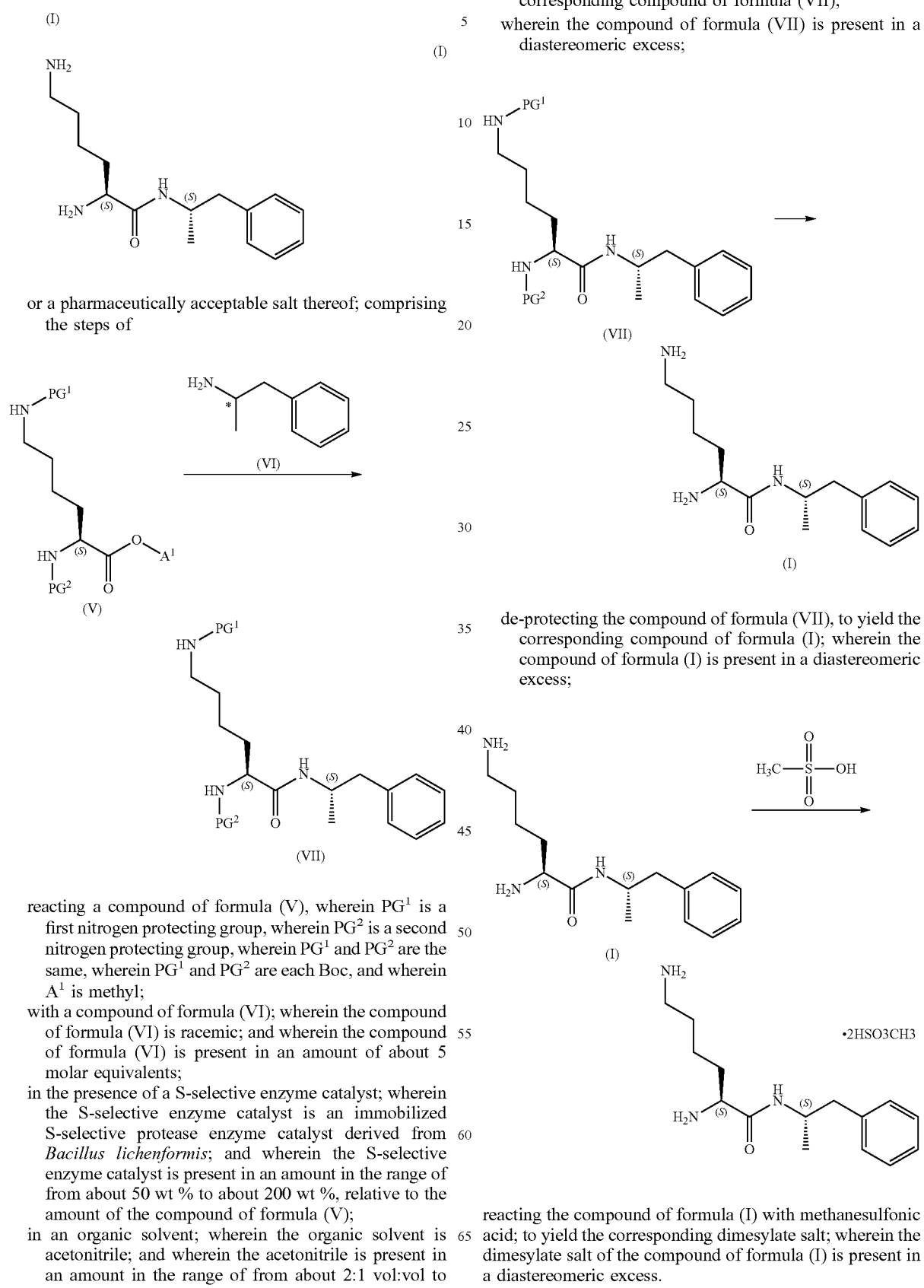

or a pharmaceutically acceptable salt thereof; comprising the steps of reacting a compound of formula (V), wherein PG¹ is a first nitrogen protecting group, wherein PG² is a second nitrogen protecting group, wherein PG¹ and PG² are the same, wherein PG¹ and PG² are each Boc, and wherein A¹ is methyl;

with a compound of formula (VI); wherein the compound of formula (VI) is racemic; and wherein the compound of formula (VI) is present in an amount of about 5 molar equivalents;

in the presence of a S-selective enzyme catalyst; wherein the S-selective enzyme catalyst is an immobilized S-selective protease enzyme catalyst derived from *Bacillus lichenformis*; and wherein the S-selective enzyme catalyst is present in an amount in the range of from about 50 wt % to about 200 wt %, relative to the amount of the compound of formula (V);

in an organic solvent; wherein the organic solvent is acetonitrile; and wherein the acetonitrile is present in an amount in the range of from about 2:1 vol:vol to about 15:1 vol:vol ratio, relative to the amount of the compound of formula (VI); at a temperature in the range of from about 30° C. to about 45° C.; to yield the corresponding compound of formula (VII);

wherein the compound of formula (VII) is present in a diastereomeric excess;

de-protecting the compound of formula (VII), to yield the corresponding compound of formula (I); wherein the compound of formula (I) is present in a diastereomeric excess;

reacting the compound of formula (I) with methanesulfonic acid; to yield the corresponding dimesylate salt; wherein the dimesylate salt of the compound of formula (I) is present in a diastereomeric excess.

26. A process for the preparation of a diastereomerically enriched compound of formula (XX)

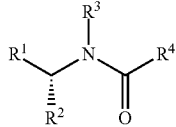
(XX)

wherein
R¹ is benzyl;
R² methyl;
R³ hydrogen;
R⁴ is an amino acid radical, wherein the amino acid is lysine;
or a pharmaceutically acceptable salt thereof; comprising

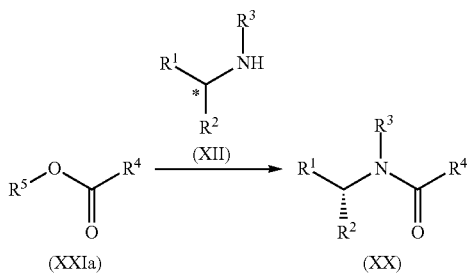

reacting a compound of formula (XXIa), wherein
R⁵ is selected from the group consisting of $C_{1-12}$ alkyl, with a compound of formula (XII); wherein the compound of formula (XII) is racemic; in the presence of an R-selective enzyme catalyst; wherein the R-selective enzyme catalyst is an immobilized R-selective protease enzyme derived from *Bacillus Lichenformis*; neat or in a solvent; to yield the corresponding compound of formula (XX); wherein the compound of formula (XX) is present in an enantiomeric excess.

27. A process for the preparation of a diastereomerically enriched compound of formula (XX)

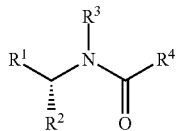
(XX)

wherein
R¹ is benzyl;
R² is methyl;
R³ is hydrogen;
R⁴ is an amino acid radical, wherein the amino acid is lysine;
or a pharmaceutically acceptable salt thereof; comprising

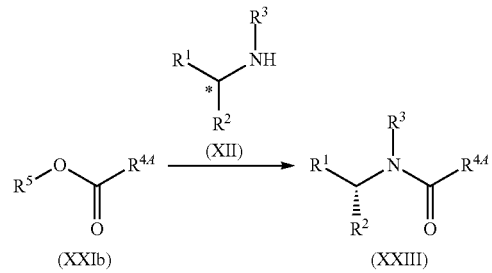

reacting a compound of formula (XXIb), wherein
$R^{4A}$ is a nitrogen-protected amino acid radical, wherein the amino acid is lysine and the nitrogen protecting group is tert-butoxycarbonyl (BOC), and wherein R⁵ is selected from the group consisting of $C_{1-12}$ alkyl, with a compound of formula (XII); wherein the compound of formula (XII) is racemic; in the presence of a R-selective enzyme catalyst; wherein the R-selective enzyme catalyst is an immobilized R-selective protease enzyme derived from *Bacillus Lichenformis*; neat or in a solvent; to yield the corresponding compound of formula (XXIII); wherein the compound of formula (XIII) is present in an enantiomeric excess;

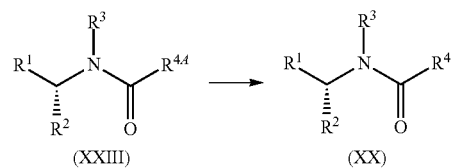

de-protecting the compound of formula (XXIII); to yield the corresponding compound of formula (XX); wherein the compound of formula (XX) is present in an enantiomeric excess.

28. A process as in claim 1, wherein said immobilized S-selective protease enzyme derived from *Bacillus lichenformis* is immobilized on a solid support.

29. A process as in claim 25, wherein said immobilized S-selective protease enzyme derived from *Bacillus lichenformis* is immobilized on a solid support.

* * * * *

UNITED STATES PATENT AND TRADEMARK OFFICE
CERTIFICATE OF CORRECTION

PATENT NO. : 10,544,434 B2  
APPLICATION NO. : 15/182698  
DATED : January 28, 2020  
INVENTOR(S) : Pietertje Elisabeth Goudriaan et al.

Page 1 of 1

It is certified that error appears in the above-identified patent and that said Letters Patent is hereby corrected as shown below:

In the Claims

Claim 1, Column 49, Line 37: "form6ula" should read -- formula --

Signed and Sealed this
Twenty-sixth Day of May, 2020

Andrei Iancu
*Director of the United States Patent and Trademark Office*